(12) United States Patent
Wohlman

(10) Patent No.: US 7,615,231 B2
(45) Date of Patent: Nov. 10, 2009

(54) METHODS FOR ENHANCING THE MORPHOLOGY, TONE, TEXTURE AND/OR APPEARANCE OF SKIN OR HAIR USING A MEADOWLACTONE

(75) Inventor: Alan Wohlman, Northbrook, IL (US)

(73) Assignee: Fan Tech, Ltd., Chicago, IL (US)

( * ) Notice: Subject to any disclaimer, the term of this patent is extended or adjusted under 35 U.S.C. 154(b) by 233 days.

(21) Appl. No.: 11/256,851

(22) Filed: Oct. 24, 2005

(65) Prior Publication Data

US 2007/0092465 A1 Apr. 26, 2007

(51) Int. Cl.
*A61K 8/02* (2006.01)
*C07D 309/00* (2006.01)

(52) U.S. Cl. ...................................... 424/401; 549/273
(58) Field of Classification Search ........................ None
See application file for complete search history.

(56) References Cited

U.S. PATENT DOCUMENTS

| | | | |
|---|---|---|---|
| 5,380,894 A | 1/1995 | Burg et al. ................. 554/219 |
| 5,646,321 A | 7/1997 | O'Lenick, Jr. .............. 554/224 |
| 5,736,571 A | 4/1998 | O'Lenick, Jr. .............. 514/549 |
| 5,741,919 A | 4/1998 | O'Lenick, Jr. .............. 554/224 |
| 5,760,260 A | 6/1998 | O'Lenick, Jr. .............. 554/224 |
| 5,786,388 A * | 7/1998 | O'Lenick, Jr. .............. 514/552 |
| 5,817,846 A | 10/1998 | O'Lenick, Jr. .............. 554/224 |
| 5,843,193 A * | 12/1998 | Hawkins et al. ................ 8/408 |
| 5,849,935 A | 12/1998 | Isbell et al. ................. 549/273 |
| 5,917,070 A | 6/1999 | O'Lenick, Jr. .............. 554/224 |
| 6,022,982 A | 2/2000 | Isbell et al. ................. 549/273 |
| 6,051,214 A | 4/2000 | Isbell et al. ............. 424/70.21 |
| 6,136,330 A * | 10/2000 | Soliman et al. ............. 424/401 |
| 6,201,143 B1 | 3/2001 | O'Lenick, Jr. .............. 554/59 |
| 6,201,144 B1 | 3/2001 | Isbell et al. ................. 554/213 |
| 6,384,248 B1 | 5/2002 | O'Lenick, Jr. .............. 549/478 |
| 6,545,052 B2 | 4/2003 | Wohlman et al. ........... 514/587 |
| 6,586,628 B2 | 7/2003 | Abbott et al. ................. 564/26 |
| 6,639,089 B2 * | 10/2003 | Ito et al. ..................... 554/115 |
| 6,653,505 B2 | 11/2003 | Abbott et al. ................. 564/26 |
| 2002/0086039 A1 | 7/2002 | Lee et al. |
| 2003/0114532 A1 | 6/2003 | Wohlman et al. |
| 2003/0204113 A1 | 10/2003 | Abbott et al. |
| 2004/0030188 A1 | 2/2004 | Abbott et al. |
| 2004/0096414 A1 * | 5/2004 | Mori et al. ................ 424/70.16 |
| 2004/0156802 A1 | 8/2004 | Iwasaki et al. |
| 2005/0069515 A1 | 3/2005 | Rivers et al. |
| 2005/0069516 A1 * | 3/2005 | Hornby et al. ................. 424/74 |
| 2005/0069517 A1 | 3/2005 | Lim et al. |
| 2005/0129632 A1 | 6/2005 | Haase et al. |

OTHER PUBLICATIONS

Isbell et al. (Synthesis of 6-eicosanolactone and 6-docosanolactone directly from meadowfoam oil. Journal of the American Oil Chemists Society vol. 78, No. 5. May, 2001.*
U.S. Appl. No. 11/256,722, filed Oct. 24, 2005, Alan Wohlman.
Information contained in an 11-page research report entitled "Research and Development Report, Meadowestolide® and Meadowlactone™, New Bio-Functional Ingredients that have Important and Measurable Skin Care Benefits" was presented at the International Federation of Societies of Cosmetic Chemists on Oct. 25, 2004.

* cited by examiner

*Primary Examiner*—Sreeni Padmanabhan
*Assistant Examiner*—Layla Soroush
(74) *Attorney, Agent, or Firm*—Roberta L. Hastreiter; Keith D. Parr; Locke, Lord, Bissell & Liddell LLP

(57) ABSTRACT

The present invention provides inexpensive, safe and reliable methods for improving the morphology, tone, texture and/or appearance of the skin and/or hair of a mammal, preferably without using one or more surfactants (or other chemicals) that can strip away, or otherwise remove, one or more protective lipids from the skin and/or hair. These methods comprise topically applying to the skin and/or hair at least three applications on a regular basis of a composition in an effective amount including: (a) a Meadowlactone in an amount that is effective for enhancing the morphology, tone, texture and/or appearance of the skin and/or hair, and having the chemical structure set forth herein; and (b) a cosmetically acceptable base in an amount that is effective for acting as a carrier vehicle for the Meadowlactone.

51 Claims, 5 Drawing Sheets
(5 of 5 Drawing Sheet(s) Filed in Color)

METHODS FOR ENHANCING THE MORPHOLOGY, TONE, TEXTURE AND/OR APPEARANCE OF SKIN OR HAIR USING A MEADOWLACTONE

BACKGROUND OF THE INVENTION

1. Field of the Invention

The present invention relates to methods for enhancing the morphology, tone, texture and/or appearance of the skin and/or hair of mammals by topically administering, or otherwise applying, effective amounts of a Meadowlactone having the chemical structure set forth herein, as an active ingredient, thereto.

2. Background

The skin and hair of mammals often become damaged or deteriorated as a result of sun exposure, exposure to chemicals, age, illness, abuse and/or similar factors. In order to eliminate or diminish lines, wrinkles, sun or age spots and/or sagging of the skin, many human beings apply a wide variety of skin care products to their skin, inject Botox (a highly purified preparation of a toxin produced by the bacterium *Clostridium botulinum*) into their skin and/or have plastic surgery (laser surgery, face lifts, eye lifts and the like). In like manner, many humans apply a variety of shampoos, conditioners and/or other haircare products to their hair in order to diminish or repair damage, dryness or deterioration of the hair, which may be caused by chemical treatments (perms, highlighting, coloring and the like), age and sun exposure. The foregoing treatments are often very expensive, and can present significant health risks to the humans, including death.

The water content of the skin stratum corneum (the outermost layer of the epidermis, or external skin surface) and surface lipids are important factors in the appearance and function of the skin. A disruption in the balance between the skin stratum corneum and surface lipids may lead to a clinical manifestation of dryness of skin. The content of hair lipids is also an important factor in the condition and appearance of hair.

The integrity of the skin and hair depends upon the continued production and maintenance of structural and active biological materials, the configuration and function of which are largely dependent upon the local environment in which they exist. This environment can be defined, in part, by the quantitative balance of oil and water in the skin tissue or hair. A primary challenge for those who strive to provide effective skin or hair care treatments is a development of ingredients and formulations that facilitate a preservation of the correct balance of lipid and aqueous components in the complex layers that comprise the epidermal surface of the skin or the outer surface of the hair. A frequent use of surfactants on a mammal's skin or hair often has a detrimental effect of stripping away, or otherwise reducing, a significant amount of protective lipids from the skin or hair, which disadvantageously enables an evaporative loss of water and a consequent dehydration of the skin or hair.

It would be beneficial to provide inexpensive, safe and reliable methods for enhancing the morphology, tone, texture and/or appearance of the skin and/or hair of a mammal without using one or more surfactants (or similar chemicals), other harsh chemicals, Botox or plastic surgery.

DESCRIPTION OF RELATED ART

Published U.S. Patent Application No. U.S. 2002/0086039 A1 describes skin and hair care products that include as a component bioactive glass (an inorganic glass material having an oxide or silicon as its major component) in a particulate form, in an aqueous solution or in a combination thereof. In contrast with the compositions employed in the methods of the present invention, and with such methods, this published patent application does not teach or suggest an application of a Meadowlactone to skin or hair, let alone a Meadowlactone having a chemical structure as described herein, a concentration of any type of lactone, let alone a concentration of a Meadowlactone having a chemical structure as described herein, or an application rate that includes more than one application of a product to skin or hair. All of the teachings and examples that are present in this published patent application disclose only one application of a product described therein to skin or hair. Further, the compositions employed in the methods of the present invention preferably do not include bioactive glass (in any form), or a composition derived from an aqueous extract of bioactive glass. While this published patent application describes meadowfoam seed oil (whole oil) as a common ingredient in lip liner products, the compositions that are employed in the methods of the invention need not include meadowfoam seed oil, or any components of meadowfoam seed oil.

Published U.S. Patent Application No. U.S. 2004/0156802A1 describes skin and hair cosmetics that comprise a chemical peeling agent, a bactericide, an anionic surfactant or a cationic surfactant and a cystine derivative, or a salt thereof, such as N,N'-diacetyl-L-cystine dimethyl ester, N-acetylcysteine or N-acetylhomocysteine. The cysteine derivative, which is stated to be capable of mitigating irritation or inflammation of the skin caused by the other components, is a required component of the cosmetics. In contrast with the compositions employed in the methods of the present invention, and with such methods, this published patent application does not teach or suggest an application of a Meadowlactone to skin or hair, let alone a Meadowlactone having a chemical structure as described herein, a concentration of any type of lactone alone (i.e., without also including a cysteine derivative, or a salt thereof), let alone a concentration of a Meadowlactone having a chemical structure as described herein, any pH values or an application rate that includes more than one application of a product to skin or hair. All of the teachings and examples that are present in this published patent application disclose only one application of a product described therein to skin or hair. Further, the compositions employed in the methods of the present invention preferably do not include cystine, a cystine derivative, or a salt thereof.

Published U.S. Patent Application No. U.S. 2005/0129632 A1 describes UV absorber compositions that are stated to be suitable as UV filters in cosmetic and pharmaceutical compositions (i.e. to protect human and animal skin and hair from the harmful effects of UV radiation). The UV absorber compositions comprise: (a) from 1 to 99% by weight of a hydroxyphenyltriazine compound of a specified formula, and (b) from 99 to 1% by weight of a further UV absorber, which is selected from a specified group. This publication describes the use of HDI/trimethylol hexyl-lactone crosspolymer in a daily care cream. In contrast with the compositions employed in the methods of the present invention, and with such methods, this published patent application does not teach or suggest an application of a Meadowlactone to skin or hair, let alone a Meadowlactone having a chemical structure as described herein, a concentration of a Meadowlactone, let alone a concentration of a Meadowlactone having a chemical structure as described herein, or an application rate that includes more than one application of a product to skin or hair. All of the teachings and examples that are present in this published patent application disclose only one application of a product described therein to skin or hair. Further, the compositions employed in the methods of the present invention preferably do not include a hydroxyphenyltriazine compound, such as those described in the published patent application, or a HDI/trimethylol hexyl-lactone crosspolymer.

U.S. Pat. Nos. 5,849,935 and/or 6,022,982, which are related, describe processes for the production of δ-lactones from $^5\Delta$, $^6\Delta$, $^9\Delta$ or $^{15}\Delta$ unsaturated fatty acids, which are either free or esterified. In contrast with the methods of the present invention, these patents do not teach or suggest the particular lactone being employed, any concentrations of any lactones in products or any application rates to a mammal's skin or hair, and do not provide any teachings, suggestions or data regarding an improvement of the morphology, tone, texture and/or appearance of a mammal's skin or hair.

U.S. Pat. No. 6,021,144 B1 describes a process for producing fatty ether esters and fatty ether acids that may be used as viscosity modifiers in creating cosmetics. Starting materials for use in the invention include one or more of a mixture of γ-, δ- or ε-lactones of a specified formula (formula III). Meadowfoam oil, having a high content of $\Delta^5$ fatty acids, is stated to be a preferred source material for preparation of the starting materials. In contrast with the methods of the present invention, this patent does not discuss skin or hair, an application of lactones to skin or hair, the concentrations of Meadowlactone described herein for application to skin or hair or the application rates described herein.

SUMMARY OF THE INVENTION

It has been surprisingly and unexpectedly determined that a lactone derived from meadowfoam (Meadowlactone) having the particular chemical structure set forth hereinbelow is particularly effective for enhancing a morphology, tone, texture and/or appearance of a mammal's skin and/or hair when employed in the manner, and under the conditions, described herein. The molecular configuration of this lactone has been found to be very dynamic, resulting in its ability to actively participate in tissue rehydration and conditioning of skin and hair. Microphotographic images of the skin of human beings that are present herein provide a clear observable visualization of the improvement that occurs in the morphology, tone, texture and/or appearance of the skin when the skin is treated with Meadowlactone in the manner described herein (preferably contained in a cream emulsion base at a level of about 2 to about 3 weight percent) in comparison with untreated skin, or with skin that has been treated with various control preparations.

The methods of the present invention advantageously provide inexpensive, safe and reliable methods for enhancing the morphology, tone, texture and/or appearance of the skin and/or hair of a mammal without the need for using one or more surfactants (or similar chemicals), other harsh chemicals, Botox or plastic surgery.

In one aspect, the present invention provides a method for enhancing a morphology, tone, texture and/or appearance of a mammal's skin comprising topically applying to the skin on a regular basis at least three applications of a composition including:
(a) a Meadowlactone in an amount that is effective for enhancing the morphology, tone, texture and/or appearance of the skin, wherein the Meadowlactone has the structure:

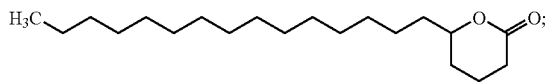

and (b) a cosmetically acceptable base in an amount that is effective for acting as a carrier vehicle for the Meadowlactone;
wherein the amount of the composition that is applied to the skin is an amount that is effective for enhancing the morphology, tone, texture and/or appearance of the mammal's skin;
wherein the pH of the composition ranges from about 2 to about 11; and
wherein the morphology, tone, texture and/or appearance of the mammal's skin is enhanced.

In another aspect, the present invention provides a method for enhancing a morphology, tone, texture and/or appearance of a mammal's skin comprising topically applying to the skin on a regular basis at least three applications of a composition consisting essentially of:
(a) a Meadowlactone in an amount that is effective for enhancing the morphology, tone, texture and/or appearance of the skin, wherein the Meadowlactone has the structure:

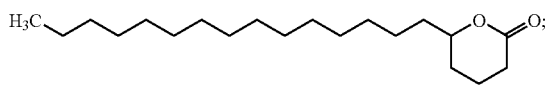

and (b) a cosmetically acceptable base in an amount that is effective for acting as a carrier vehicle for the Meadowlactone;
wherein the amount of the composition that is applied to the skin is an amount that is effective for enhancing the morphology, tone, texture and/or appearance of the mammal's skin;
wherein the pH of the composition ranges from about 2 to about 11; and
wherein the morphology, tone, texture and/or appearance of the mammal's skin is enhanced.

In still another aspect, the present invention provides a method for enhancing a morphology, tone, texture and/or appearance of a mammal's hair comprising topically applying to the hair at least three applications of a composition including:
(a) a Meadowlactone in an amount that is effective for enhancing the morphology, tone, texture and/or appearance of the hair, wherein the Meadowlactone has the structure:

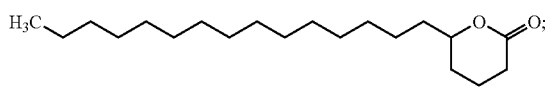

and (b) a cosmetically acceptable base in an amount that is effective for acting as a carrier vehicle for the Meadowlactone;

wherein the amount of the composition that is applied to the hair is an amount that is effective for enhancing the morphology, tone, texture and/or appearance of the mammal's hair;

wherein the pH of the composition ranges from about 2 to about 11; and wherein the morphology, tone, texture and/or appearance of the mammal's hair is enhanced.

In yet another aspect, the present invention provides a method for enhancing a morphology, tone, texture and/or appearance of a mammal's hair comprising topically applying to the hair at least three applications of a composition consisting essentially of:

(a) a Meadowlactone in an amount that is effective for enhancing the morphology, tone, texture and/or appearance of the hair, wherein the Meadowlactone has the structure:

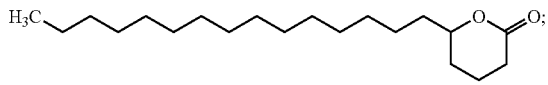

and (b) a cosmetically-acceptable base in an amount that is effective for acting as a carrier vehicle for the Meadowlactone;

wherein the amount of the composition that is applied to the hair is an amount that is effective for enhancing the morphology, tone, texture and/or appearance of the mammal's hair;

wherein the pH of the composition ranges from about 2 to about 11; and wherein the morphology, tone, texture and/or appearance of the mammal's hair is enhanced.

It is preferred that a Meadowlactone having the chemical structure set forth herein is the only active agent (compound or substance that has an ability to produce an observable or otherwise detectable effect upon a mammal's skin and/or hair) that is employed in the compositions that are used in the methods of the present invention.

The compositions that are employed in the methods of the invention, and such methods, are safe for use by mammals and typically do not irritate the mammals' skin or scalp.

BRIEF DESCRIPTION OF THE DRAWINGS

The patent or application file contains at least one drawing and/or photograph executed in color. Copies of this patent or patent application publication with color drawing(s) and/or photograph(s) will be provided by the Office upon request and payment of the necessary fee.

DETAILED DESCRIPTION OF THE PREFERRED EMBODIMENTS

Figure 1:
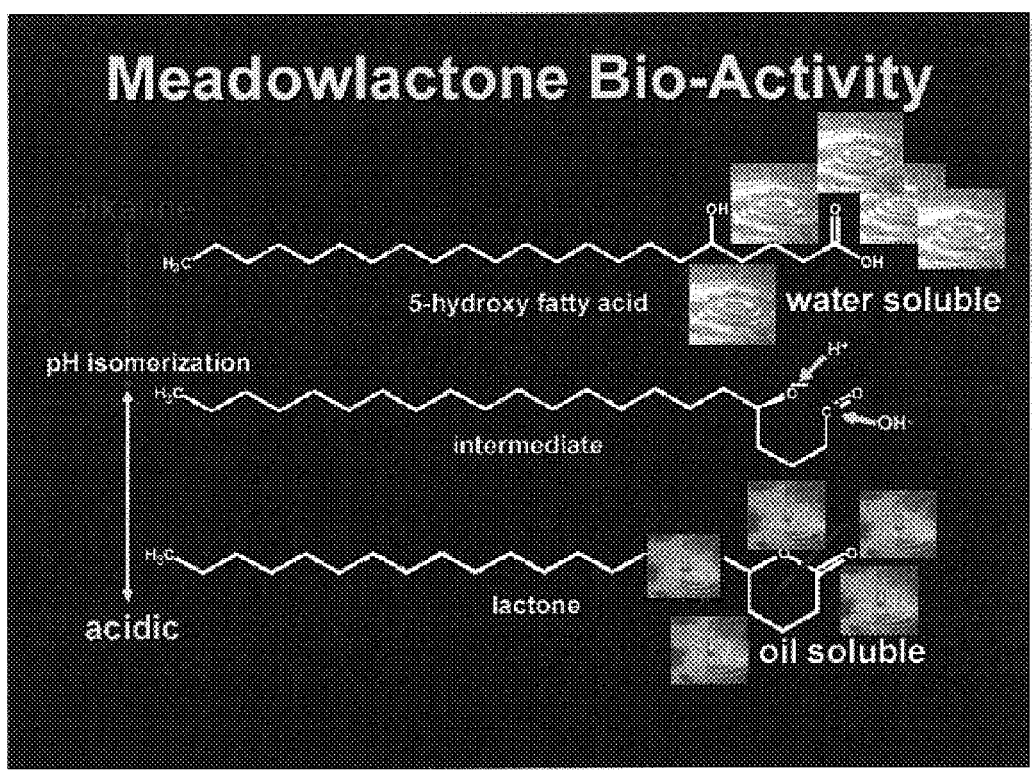
FIG. 1 is a diagram showing the dynamic equilibrium between water-soluble and oil-soluble forms of Meadowlactone at an alkaline, neutral and acid pH, and Meadowlactone bioactivity, resulting from the physical chemistry experiments that are described in Example 3.

The present invention may be understood more readily by reference to the following detailed description of the preferred embodiments of the invention, and to the examples included therein.

Definitions

For purposes of clarity, various terms and phrases used throughout this specification and the appended claims are defined in the manner set forth below. If a term or phrase used in this specification, or in the appended claims, is not defined below, or otherwise in this specification, the term or phrase should be given its ordinary meaning.

The phrase "antioxidant agent" as used herein means an agent that has an ability to prevent, reduce or aid in the prevention or reduction of, an oxidation, degradation and/or other decomposition of one or more ingredients or components, such as a fat or an oil, and/or to prevent, or aid in the prevention of, oxygen-based damage to hair, skin or other cells. Antioxidant agents include, for example, various tocopherol mixtures, edible acids (citric acid, ascorbic acid and the like), vitamin A, vitamin C, vitamin E, beta-carotene, selenium, magnesium, herbal extracts, such as a Rosemary, Sage, Oregano, Ginger, Marjoram or Rosemary Oleoresins extract, plant phenols, such as Vanillin, ellagic acid and Resveratrol, and synthetic antioxidants, such as tertiary butylhydroquinone (TBHQ), butylated hydroxyamisole (BHA) or butylated hydroxytoluene (BHT), or mixtures thereof.

The phrase "carrier vehicle" as used herein means a medium for providing a controlled delivery of an active agent to a mammal, or part thereof, such as the skin.

The term "component" as used herein means a part, portion, element, constituent or ingredient, and is used interchangeably with "ingredient." For example, in connection with a composition employed in the methods of the invention, this term means an ingredient, or combination of ingredients, used in the composition, or a part, portion, element or constituent thereof, depending upon the context in which this term is used, which may readily be determined by those of skill in the art.

The phrase "cosmetically acceptable base" as used herein means a base that can serve as a carrier vehicle for a Meadowlactone having the chemical structure described herein, and that may be applied to the skin or hair of a normal and healthy mammal in a reasonable quantity over a reasonable period of time, preferably without an unreasonable risk of harm, injury, inflammation, irritation or allergic response to, or by, the skin or hair, or illness or harm to the mammal. Persons of ordinary skill in the art may readily determine whether or not a particular base is a cosmetically acceptable base.

The phrase "inexpensive" as used herein means relatively inexpensive in comparison with other methods that attempt to achieve the same or similar results.

The term "cystine" as used herein means an amino acid, $C_6H_{12}N_2O_4S_2$, that generally is formed from the disulfide linkage of two cysteines during folding of many proteins, especially keratin, and stabilizing the tertiary structure of the protein.

The phrase "diluent" as used herein means a substance or agent that dilutes, facilitates a physical separation of one or more ingredients and/or makes thinner or weaker. Diluent materials that are suitable for use with mammals could generally include complex polysaccharides, carbohydrates, smaller sugars (dextrose, sucrose and the like), dicalcium phosphate, tricalcium phosphate, maltodextrin and water.

The phrase "does not irritate the mammal's skin" as used herein means that a composition employed in the methods of the invention, and such methods, does not result in a significant amount of detectable irritation (redness, burning, itching, adverse change in skin surface, inflammation and/or chafing) to the skin of an average, healthy mammal that does not have, or suffer from, or have a history or having, or suffering from, any significant (or any) skin allergies or diseases (including allergic hypersensitivity). Skin irritation and allergic hypersensitivity may be determined using standard methods and equipment known by those of skill in the art.

The phrase "does not irritate the mammal's scalp" as used herein means that a composition employed in the methods of the invention, and such methods, does not result in a significant amount of detectable irritation (redness, burning, itching, adverse change in scalp surface, inflammation and/or chafing) to the scalp (skin covering the head of a mammal) of an average, healthy mammal that does not have, or suffer from, or have a history or having, or suffering from, any significant (or any) skin allergies or diseases (including allergic hypersensitivity). Skin irritation and allergic hypersensitivity may be determined using standard methods and equipment known by those of skill in the art.

The term "emulsifier" as used herein means any substance or agent that aids in the formation of an emulsion, such as egg yolk, egg lecithin, soy lecithin and mono- and di-glycerides.

The term "emulsion" as used herein means a generally stable and homogeneous mixture of two liquids that do not normally mix (i.e., they are immiscible between themselves), such as vegetable oil and water, for example, milk and mayonnaise. Emulsions can be true colloids or less stable mixtures, such as salad dressing, which tend to separate in a short time. An emulsion can often be broken down (i.e. the liquids separated) by factors such as mechanical manipulation, chemical effects and/or time.

The phrase "enhancing the morphology, tone, texture and/or appearance of the skin of mammals" as used herein means, in mammals that do not have a significant skin disease, having an observable or otherwise detectable elimination or reduction in the quantity and/or severity of skin lines, wrinkles, sagging, spots, bumps, blisters, dryness, redness (or other discoloration) or other defects, deformations, and/or damage resulting from sun exposure, exposure to chemicals, exposure to oxygen, age, illness, abuse and/or similar factors, increase in the taughtness/tightness or smoothness of the skin or increase in a youthful appearance of the skin. An enhancement in the morphology, tone, texture and/or appearance of the skin of a mammal may be detected visually, manually (by touch or feel) or using techniques known by those of skill in the art, by comparing the skin as it existed prior to applications of a composition thereto with the same skin as it exists after applications of a composition thereto.

The phrase "enhancing the morphology, tone, texture and/or appearance of the hair of mammals" as used herein means, in mammals that do not have a significant skin disease, having an observable or otherwise detectable elimination, or reduction in an amount, of dryness, brittleness, quantity of split ends, or of other defects deformations, and/or damage of the hair, or of one or more strands thereof, resulting from sun exposure, exposure to chemicals, exposure to oxygen, age, illness, abuse and/or similar factors or an increase in the volume, strength, softness, body and/or shine of the hair. An enhancement in the morphology, tone, texture and/or appearance of the hair of a mammal may be detected visually, manually (by touch or feel) or using techniques known by those of skill in the art, by comparing the hair as it existed prior to applications of a composition thereto with the same hair as it exists after applications of a composition thereto.

The term "fat" as used herein means any of the various saturated and/or unsaturated (including monounsaturated and polyunsaturated), hydrogenated or unhydrogenated soft solid, semisolid and/or solid organic compounds that generally comprise the glyceride esters of fatty acids and associated phosphatides, sterols, alcohols, hydrocarbons, ketones and/or related compounds, components thereof and/or mixtures or other combinations thereof. Such components include, but are not limited to, fatty acids, glycerides (mono-, di- and tri-), ethyl and other esters of fatty acids, as well as components thereof, and combinations thereof. Fats occur widely in organic tissue, particularly in the subcutaneous connective tissue of animals (beef, poultry, pork, lamb, liver and the like), and in the seeds, nuts and fruits of plants. There is generally no chemical difference between fats and oils, with the only distinction being that fats are generally solid at room temperature and oils are generally liquid at room temperature.

The phrase "fatty acids" as used herein means carboxylic acids that generally are derived from, or contained in, an animal, vegetable or other fat or oil, whether saturated, unsaturated, monounsaturated, polyunsaturated, aromatic, essential, nonessential, in a cis or trans form, in the ethyl esters, mono-, di- or tri-glycerides, free fatty acids or other forms, and components and combinations of the foregoing. Fatty acids include, but are not limited to, the specific fatty acids identified below:

| Common Name | Number of Carbon Atoms | Number of Double Bonds |
| --- | --- | --- |
| Butyric Acid | 4 | 0 |
| Caproic Acid | 6 | 0 |
| Caprylic Acid | 8 | 0 |
| Capric Acid | 10 | 0 |
| Lauric Acid | 12 | 0 |
| Myristic Acid | 14 | 0 |
| Palmitic Acid | 16 | 0 |
| Palmitoleic Acid | 16 | 1 |
| Stearic Acid | 18 | 0 |
| Oleic Acid | 18 | 1 |
| Linoleic Acid | 18 | 2 |
| Alpha-Linolenic Acid (ALA) | 18 | 3 |
| Gamma-Linolenic Acid (GLA) | 18 | 3 |
| Arachidic Acid | 20 | 0 |
| Gadoleic Acid | 20 | 1 |
| Arachidonic Acid (AA) | 20 | 4 |
| Eicosapentaenoic Acid (EPA) | 20 | 5 |
| Behenic Acid | 22 | 0 |
| Erucic Acid | 22 | 1 |
| Docosahexaenoic Acid | 22 | 6 |
| Lignoceric Acid | 24 | 0 |

Other fatty acids are known by those of skill in the art. A wide variety of fatty acids are commercially available from sources known by those of skill in the art. Also, oils can be separated into their component fatty acids on a capillary column in a gas chromatograph, and the relative fatty acid contents measures. Additional information concerning fatty acids is readily available from the Fatty Acid Producer's Council (New York, N.Y.).

The term "humans" as used herein, unless otherwise stated, includes human beings that are babies, infants, children or adults.

The abbreviation "INCI" as used herein means International Nomenclature Cosmetic Ingredient.

The term "ingredient" is used herein interchangeably with "component" in connection with compositions described herein.

The term "lactone" as used herein means an anhydride formed by the removal of a water molecule from the hydroxyl and carboxyl radicals of hydroxy acids.

The phrase "leave-on" means a composition or product that is applied to the skin or hair without a deliberate rinsing step within a specified period of time after its application to the skin or hair.

The term "lipid" as used herein means any of a group of organic compounds, including fats, oils, waxes, sterols, and triglycerides, that generally are insoluble in water but soluble in nonpolar organic solvents, are oily to the touch, and together with carbohydrates and proteins constitute the principal structural material of living cells.

The phrase "liquid" as used herein means a fluid or semi-fluid, the shape of which is generally determined by the container that it fills.

The term "mammals" as used herein includes humans and non-human mammals.

The phrase "marine oil" as used herein includes, but is not limited to, "fish oil" and one or more individual components of marine oil, such as an omega-3 fatty acid, or a combination thereof. Marine oils include, for example, herring oil, cod oil, anchovy oil, tuna oil, sardine oil, menhaden oil and algae oil.

The terms "Meadowlactone" and "meadowfoam lactone" as used herein mean a lactone derived from meadowfoam, such as from an unsaturated fatty acid that is present in meadowfoam seed oil.

The term "oil" as used herein means a fat that generally is viscous, liquid or liquefiable at room temperature, and includes mixtures and other combinations of one or more oils and/or components of oils, such as fatty acids, glycerides and/or ethyl esters of fatty acids (or components thereof).

The phrase "on a regular basis" as used herein means that a composition employed in the methods of the invention is applied to the skin or hair of a mammal on a reasonably continuous basis (i.e. without delaying one or more applications for an unreasonably lengthy period of time), for example, a regular application of the composition to the mammal's skin or hair one, two, three, four, five, six, seven, eight, nine, ten and so forth times within a period of one, two, three, four, five, six, seven, eight, nine, ten and so forth days for a duration of one, two, three, four, five, six, seven, eight, nine, ten and so forth days or weeks.

The phrase "plant seed oil" as used herein means an oil that is extracted, or otherwise obtained from, a seed of a plant, either directly or indirectly, particularly oily seeds, including one or more individual components thereof and mixtures thereof. Plant seed oils include, but are not limited to, Black Currant seed oil, Borage seed oil, safflower seed oil, sunflower seed oil, sesame seed oil, avocado seed oil, pumpkin seed oil, olive seed oil, coconut seed oil, rapeseed oil, flaxseed (linseed) oil, cottonseed oil, meadowfoam seed oil, tung oil, parsley seed oil, carrot seed oil, fennel fruit oil, parsnip seed oil, coriander seed oil, chervil seed oil, caraway plant oil and celery seed oil. Other plant seed oils are known by those of skill in the art.

The phrase "plant oil" as used herein means an oil that is extracted, or otherwise obtained from, a plant, either directly or indirectly, particularly oily plants, including one or more individual components thereof and mixtures thereof. Plant oils include, but are not limited to, Evening Primrose oil, Borage oil, safflower oil, sunflower oil, peanut oil, walnut oil, almond oil, avocado oil, olive oil, corn oil, soy oil, soybean oil, coconut oil, palm oil, palm kernel oil and castor oil. Other plant oils are known by those of skill in the art.

The term "plurality" as used herein means more than one, such as two, three, four, five, six, seven, eight, nine, ten, fifteen, twenty or the like.

The abbreviation "q.s." as used herein means a sufficient quantity, for example, to cause the weight percent of a composition to be 100%, or to obtain a desired effect or benefit.

The phrase "rinse-off" means a composition or product that is applied to the skin or hair with a deliberate rinsing step within a specified period of time after its application to the skin or hair, for example, one, two, three, five, ten, fifteen, twenty, thirty, forty or forty-five minutes after being applied to the skin or hair.

The phrase "room temperature" as used herein means the temperature in a room, which generally ranges from about 15° C. to about 30° C. (from about 59° F. to about 86° F.), and more usually ranges from about 21° C. to about 23° C. (from about 70° F. to about 74° F.). The "ambient temperature" of a room is "room temperature."

The phrase "safe for use" in connection with compositions described herein, and methods of the invention, means that the compositions, and the components contained therein, and the methods, using reasonable quantities of active and other components, and administered for reasonable periods of time (such as those quantities and periods of time described herein, or as otherwise recommended for a particular mammal by a physician, veterinarian or other skilled clinician), which may vary for different types of mammals, do not cause, or present an unreasonable risk of harm, damage, defect, disorder, deformity or injury to, or by, the skin, scalp or hair of an average, healthy mammal that does not have, or suffer from, or have a history or having, or suffering from, skin or scalp allergies or diseases, or illness, disease or harm to an average, healthy mammal that does not have, or suffer from, or have a history or having, or suffering from, skin or scalp allergies or diseases. Preferably, such compositions and methods do not cause, or present, virtually any (or any) such risk.

The term "skin" as used herein in connection with human beings means the outer integument or covering of the body, generally consisting of the corneum, or dermis, and the epidermis, for example, the outer covering of the face (typically not including the lips) or the outer covering of the neck. In connection with non-human mammals, the term "skin" means the outer covering of the body that is not fur.

The phrases "surfactant" and "wetting agents" as used herein mean substances or agents that lower the surface tension (tendency of a liquid to reduce its exposed surface to the smallest possible area) of a liquid, generally allowing easier spreading, and/or the interfacial tension between two liquids. Surfactants are usually organic compounds that are amphipathic in that they contain both hydrophobic groups (their "tails") and hydrophilic groups (their "heads"). Therefore, they are typically sparingly soluble in both organic solvents and water. Surfactants generally reduce the surface tension of water by adsorbing at the air-water interface, and reduce the interfacial tension between oil and water by adsorbing at the liquid-liquid interface. Many surfactants can also assemble in the bulk solution into aggregates that are known as micelles.

The phrases "topical administration" and "topically applying" as used herein mean an application onto the skin or hair (generally onto one or more exposed or outer surfaces thereof, such as the epidermis), for example, using hands, fingers or a wide variety of applicators (spray, pump, brush, mat, powder puff, cotton ball, cue tip and the like). The application may be made, for example, by laying, pouring, spreading, spraying, sprinkling or massaging into, or onto, the skin or hair, or by any other convenient or suitable method.

As used herein, the term "viscosity" means resistance to flow (of a fluid or semi-fluid). Viscosity can be measured using, for example, a commercially available viscometer.

The term "wax" as used herein means a fatty substance that generally is solid at room temperature and softens and melts when warmed. Generally, waxes are similar in composition to fats and oils, with the exception that they do not contain glycerides. Some waxes are hydrocarbons, and others are esters of fatty acids and alcohols. Examples of waxes include, but are not limited to, beeswax, lanolin, carnauba, candelilla, ozokerite, bayberry, sugar cane, paraffin, microcrystalline and sorbitol.

General Description and Utility

The present invention provides cost-effective methods that are useful for enhancing the morphology, tone, texture and/or appearance of the skin and/or hair, preferably without using any surfactants or other chemicals that can strip away one or more protective lipids of the skin or hair, and that are safe for use by mammals. Such methods can be employed by skin and/or hair care professionals, such as dermatologists, as well as by individuals, to enhance the morphology, tone, texture and/or appearance of the skin and/or hair.

With respect to treatment of hair, a user may apply a composition employed in the methods of the invention to the hair, for example, by massaging or rubbing the composition into the hair and, if the product is not to be left on the hair, to rinse the hair with water following application.

Meadowlactone

Meadowfoam, or *Limnanthes alba*, is a white flowered, herbaceous plant which gets its name because of its resemblance to a meadow of foam when blooming. The naturally-occurring oil that can be extracted from the seeds of meadowfoam (known as "meadowfoam oil" or "meadowfoam seed oil"), using techniques known by those of skill in the art, contains over 98% of long-chain fatty acids, predominantly as triglycerides. Meadowfoam seed oil has a high content of $\Delta^5$ unsaturated fatty acids (total fatty acids composed of approximately 60% 5-eicosenoic acid, 10% 5-docosenoic acid, 19% 5,13-docosadienoic acid, and less than 5% 18:1 $\Delta^5$ fatty acids). Meadowfoam seed oil is commercially available, for example, from The Fanning Corporation (Chicago, Ill.) and Botagenics, Inc. (Northridge, Calif.).

Meadowfoam seed oil lactones are one class of hundreds of different types of compounds or derivatives that may be obtained, or derived, from meadowfoam seed oil. The meadowfoam seed oil lactone (Meadowlactone) having the chemical structure described herein, which is a delta-lactone, is one of hundreds of different types of meadowfoam seed oil lactones that may be derived from meadowfoam seed oil.

The Meadowlactone that is employed in the methods of the invention is a spatially oriented compound that can aid in reestablishing a physiologically correct balance of oil and water in epidermal tissue and hair and, thereby, restore skin and hair to a healthy, youthful morphology. This Meadowlactone is an amphoteric compound having isomeric structures that can shift between oil and water solubility as a function of pH.

The Meadowlactone that is employed in the methods of the invention, when applied to skin and/or hair in reasonably low concentrations, such as in a skin or hair cream base including from about 1 to about 5 weight percent of Meadowlactone, generally produces a marked sensory improvement in both the feel and appearance of the skin and/or hair, and in the skin tone and texture thereof. It has been surprisingly and unexpectedly determined as a result of a significant amount of experimentation that the methods of the present invention, which employ compositions that include a Meadowlactone having a particular chemical structure, achieve superior results in comparison with the same or similar methods that include meadowfoam oil (crude or refined).

The Meadowlactone that is employed in the methods of the present invention is commercially available from The Fanning Corporation (Chicago, Ill.). Alternatively, the Meadowlactone can be produced from meadowfoam seed oil using methods and equipment known by those of skill in the art. Processes for producing lactones from unsaturated fatty acids are, for example, described in U.S. Pat. Nos. 5,894,935 and 6,022,982. The Meadowlactone is an anhydride formed by the removal of a water molecule from the hydroxyl and carboxyl radicals of hydroxy fatty acids.

Generally, methods for producing meadowfoam seed lactones include the steps of: (1) crushing (preferably to a flaked condition) the seeds of the plant *Limnanthes alba*; (2) washing the seeds with a solvent, whereby the oil from the seed becomes dissolved in the solvent; (3) separating the spent seeds and the solvent solution; (4) treating the solvent solution, for example, using distillation techniques, to remove the solvent from the oil extract; (5) deodorizing the oil extract; (6) hydrolyzing the oil extract to obtain free fatty acids present in the oil extract; (7) distilling the fatty acids; (8) reacting the fatty acids to lactones; and (9) recovering lactones. All of the foregoing steps may be performed using conventional techniques and equipment. Hydrolysis of the oils to the fatty acids may be achieved, for example, using conventional splitting techniques, alkali splitting of fats or splitting with steam under pressure. Suitable alkali splitting techniques include, for example, treatment with sodium methoxide or sodium or potassium hydroxide. See, for example, published U.S. Patent Application No. 2005/0042347 A1, which describes a method for producing an oil extract from the seeds of meadowfoam plants, U.S. Pat. Nos. 5,849,935 and 6,022,982 and "A.O.C.S. Tentative Method Ca-6b-53" in Official and Tentative Methods of the American Oil Chemist's Society, third edition, AOCS, Chicago, Ill. (1973).

Techniques for the synthesis of lactones have been described throughout the chemical literature, and have included acid catalyzed reactions of unsaturated or olefinic acids. A variety of acids, such as $H_2SO_4$, methanesulfonic acid or trifluoromethane sulfonic acid, will catalyze a reaction of fatty acids to lactones. For example, U.S. Pat. Nos. 5,849,935 and 6,022,982 describe processes for the production of δ-lactones from $\Delta^5$, $\Delta^6$ or $\Delta^9$ to $\Delta^{15}$ (having a double bond between $\Delta^9$ and $\Delta^{15}$) unsaturated fatty acids (in either a pure or a mixed form), such as oleic acid (18:1 $\Delta^9$), palmitoleic acid (16:1 $\Delta^9$), linoleic acid (18:2 $\Delta^{9,12}$), erucic acid (22:1 $\Delta^{13}$) and linolenic acid (18:3 Δ9,12,15), which are either free or esterified with glycerol or other aliphatic alcohols (methanol, ethanol, isopropanol or branched chain alcohols). One or more $\Delta^5$, $\Delta^6$ or $\Delta^9$ to $\Delta^{15}$ unsaturated fatty acids is reacted in the presence of an acid, clay or zeolite catalyst, such as $HBrO_4$, $HIO_4$, $H_2SO_4$ and $H_2ClO_4$ in a concentration of between about 0.5 to 10 molar equivalents and at a temperature between about 20 and 70° C. Starting materials include free and esterified unsaturated fatty acids having the formula $R_1$—CH=CH—$(CH_2)_n$—$COOR_2$, wherein n is an integer between 7 and 13, $R_1$ is hydrocarbon and $R_2$ is H, an aliphatic hydrocarbon or a glyceride moiety which, in combination with the fatty acid, comprises a mono-, di- or triglyceride. Additionally, Isbell and Plattner (JAOCS 74:153-158, 1997) have described a process for the production of δ-lactones from $\Delta^5$ unsaturated fatty acids, such as eicosenoic acid, which is present in meadowfoam oil. Selective synthesis of δ-lactones is accomplished by reaction of the $\Delta^5$ fatty acid in a highly polar solvent in the presence of an acid catalyst at low temperatures. Selectivity for the δ-lactone over the y-lactone is favored by using lower temperatures, low acid concentrations and high solvent ratios.

It is preferred that the Meadowlactone that is employed in the methods of the invention is employed in a substantially pure form, and that no other components of, or compounds contained in, meadowfoam oil (crude or refined), and no meadowfoam oil, are employed in these methods, or are included in the compositions that are employed in these methods. Methods for purifying Meadowlactones are known by those of skill in the art. It is also preferred that no active agents, substances or compounds (agents, substances or compounds that, in large enough quantities, have an ability to produce an effect or change to the morphology, tone, texture and/or appearance of the skin or hair of a mammal), from any source, other than the Meadowlactone, are included in the compositions that are employed in the methods of the invention.

The total amount of the Meadowlactone having the chemical structure described herein that is effective for enhancing the morphology, tone, texture and/or appearance of the skin and/or hair of a mammal may vary widely, depending upon a variety of factors, such as the type, age, sex, genetic predisposition and general health of the mammal, as well as the mammal's sun exposure, and the type and formulation of the particular base being employed, and may readily be determined by those of skill in the art. Typically, a total amount of from about 0.10 to about 20 weight percent, based upon the total weight of the compositions, of the Meadowlactone is present in the compositions that are employed in the methods of the invention. For example, the weight percent of the Meadowlactone may be about one, two, three, four, five, six, seven, eight, nine, ten, eleven, twelve, thirteen, fourteen, fifteen, sixteen, seventeen, eighteen, nineteen or twenty. The amount of the Meadowlactone preferably ranges from about 1 to about 5 weight percent, and more preferably ranges from about 1.5 to about 4.5 weight percent, and even more preferably ranges from about 2.0 to about 4.0 weight percent, and most preferably ranges from about 2.5 to about 3.5 weight percent. The amount of the Meadowlactone, in some cases, may range from about 0.10 to about 4 weight percent and, in other cases, may range from about 6 to about 20 weight percent.

Cosmetically Acceptable Base

A wide variety of cosmetically acceptable bases, which may be employed as carrier vehicles, diluents or dispersants for the active ingredient (Meadowlactone) that is employed in the compositions that are used in the methods of the invention, are known by those of skill in the art, and are commercially available from sources known by those of skill in the art, such as The Fanning Corporation (Chicago, Ill.). For example, a variety of cosmetically acceptable bases are described in "Cosmetic Additives—An Industrial Guide" (William Andrew Publishing, 1991), "Cosmetic and Toiletry Formulations" (Volume 3, $2^{nd}$ Edition, William Andrew Publishing, 1995), "Handbook of Cosmetics and Personal Care" (Gower Publishing Unlimited, ISBN 0566074702, 1994), "Cosmetic Ingredients" (Three Rivers Press, ISBN 0609803670, 1999) and "Cosmetics Unmasked" (Thorsons, Harper Collins, ISBN 0-00-710568-1, 2001), or are commercially available from Base Formula, Ltd. (Melton Mowbray, England), Well Naturally Products, Ltd. (Blaine, Wash.), Essential Wholesale (Clackamas, Oreg.), Urist Cosmetics, Inc. (Richmond, Calif.) and Sciencelab.com, Inc. (Houston, Tex.).

Ingredients that may generally be included in and/or used to produce a cosmetically acceptable base include, but are not limited to, any suitable combination and amounts of cosmetically acceptable ingredients, which may readily be determined by those of skill in the art, such as the following, as well as those that are described in the Examples set forth hereinbelow:

Glycols

Glycerin
Propylene Glycol
Butylene Glycol
Hexylene Glycol
2-Methyl Propane Diol

-continued

Alcohols

Ethanol
Isopropanol
n-propanol
lauryl alcohol
oleyl alcohol
Esters

Isopropyl Myristate
Isopropyl Palmitate
Jojoba Oil
Glyceryl tri caprate/caprylate
Propylene Glycol di Caprate/Caprylate
Sorbitan Esters
Diesters of Diacids
Ethyl Acetate
Butyl Acetate
Ethoxylated Materials Ethoxylated Fatty Alcohols
Ethoxylated Fatty Acids
Ethoxylated Sorbitan Esters
Ethoxylated Glycerides
Ethoxydiglycol
Aerosol Propellants Propane
Butane
Pentane
Isobutane
HFC, CFC, HCFC
Waxes/Bases Lubragels
Zigels
Jojoba Glaze
Absorption Bases
Ketones Acetone
Methyl Ethyl Ketone
Propoxylated Materials Propoxylated Fatty Alcohols
Propoxylated Fatty Acids
Esters of Propoxylated Fatty Alcohols
Ethoxylated Propoxylates
Aerosol Propellant Gases
Anhydrous Ionic Surfactants Phosphate Esters
Sulfates
Carboxylates
Fatty Amine Salts
Quaternary Nitrogen Salts
Fats, Oils and Waxes Derived from Animals, Plants, Seeds,
Minerals, Marine or Other Sources
Silicones Dimethicone
Simethicone
Cyclomethicone
Dimethicone Ethoxylates and
and Propoxylates
Fluorocarbons and Derivatives Zonyls
Fluorocarbon Alcohols
Amides Fatty Acid Diethanolamides
Fatty Acid Monoethanolamides
Fatty Acid Dimethylaminopropyl
Amides
Polymers -continued Polyalkenes
Polyoxethylenes
Polyoxypropylenes
Polyamides
Polyesters
Polyurethanes
Cellulostics and Derivatives
Copolymers
Aliphatic Compounds n-alkanes
branched alkanes
Permethyls Methods, equipment, techniques and ingredients that are generally employed in the preparation of skin and/or hair care products or components, such as cosmetically acceptable bases, are well known by those of skill in the art. For example, shampoos, hair detangling products, hair mousses, hair sprays and other hair care products often contain water, mineral oil, lanolin, stearic acid, citric acid, ammonium lauryl sulfonate, triethanolamine, lauramide DEA, lecithin, glycol stearate, cetyl alcohol, methylparaben, methylisothiozoline, xanthan gum, fragrance and/or various coloring agents.

The amount of a cosmetically acceptable base that is included in the compositions that are employed in the methods of the invention is an amount that is effective for acting as a carrier vehicle, diluent or dispersant for the Meadowlactone. Such amount will generally be 100 weight percent (total weight of the composition) minus the total weight percent of the Meadowlactone, and typically ranges from about 80 to about 99.9 weight percent, based upon the total weight of the compositions. For example, the weight percent of the Meadowlactone may be about eighty, eighty-one, eighty-two, eighty-three, eighty-four, eighty-five, eighty-six, eighty-seven, eighty-eight, eighty-nine, ninety, ninety-one, ninety-two, ninety-three, ninety-four, ninety-five, ninety-six, ninety-seven, ninety-eight or ninety-nine. Such an amount preferably ranges from about 95 to about 99 weight percent, more preferably ranges from about 95.5 to about 98.5 weight percent and most preferably ranges from about 97.5 to about 96.5 weight percent. The amounts of the various ingredients that may be present in the base may vary widely depending upon a variety of factors, such as the number of ingredients that are employed, the type of ingredients that are employed, whether the base is being employed for a skin or hair care product and the like, and may readily be determined by those of ordinary skill in the art.

One formula for a skin base cream (a skin cream emulsion base) that may be employed in the methods of the invention contains the components set forth below, and the concentrations thereof.

| Component | Weight Percent |
|---|---|
| Deionized water | 87.0-90.0% |
| Self-emulsifying wax N.F. (Fancor ® SEW-P)* | 7.75% |
| Methylparaben/propylparaben (preservative) | 0.25% |

*Available from The Fanning Corporation (Chicago, IL).

This base is prepared by separately heating the self-emulsifying wax and the water, containing preservatives, to about 80 degrees centigrade. Then, the oil phase (melted wax) is added slowly to the water phase with vigorous mixing. While mixing, the mixture is cooled. The cream begins to set up as the mixture cools. The mixture is continued cooling until the product reaches about 40 degrees centigrade. Mixing is then discontinued, and the product forms by standing at room temperature.

Water

The amount of water (deionized, saline, tap or other) that may be used in compositions that are employed in the methods of the invention may vary widely depending upon the form of the compositions. Generally, for those forms of the compositions that include water, such as shampoos or liquid cosmetic foundations, the amount of water that is employed is an amount that is effective for raising the total weight of the composition to 100 percent, and to provide the composition with a desired viscosity. This amount generally ranges from about 50 to about 90 weight percent of the total weight of the compositions, and preferably ranges from about 70 to about 80 weight percent, with about 75 weight percent being most preferred.

Optional Ingredients

The compositions that are employed in the methods of the invention may, in some cases, optionally, contain one or more other active or inactive ingredients, such as various vitamins, minerals, antioxidants, anti-inflammatory agents, antibacterial agents, antiviral agents, whitening agents, thickening agents (xanthan gum, guar gum, gum arabic, methylcellulose, sodium carboxymethyl cellulose, carrageenan, starch and the like), dispersing agents, anti-itch agents, polymers, pigments, emollients, cell activating agents, surfactants, emulsifiers, solvents (water, brine, polyethylene, glycerol, glycerine, mineral oil, other oils and the like), preservatives, sunscreen agents, perfume agents, colorants, collagen, glycerin, stearic acid, glycol stearate, lecithin, cetyl alcohol, talc, petrolatum jelly, cocoa butter, aloe vera, lanolin or other agents, for example, vitamin E ($\alpha$-tocopherol, $\beta$-tocopherol, y-tocopherol, $\delta$-tocopherol and the like). However, the compositions need not include any ingredients other than the Meadowlactone (active agent) and base (including one or more inactive ingredients).

Viscosity

The viscosity of the compositions that are employed in the methods of the invention, when in the form of a liquid or semi-liquid, may vary widely, depending upon the components that are present therein, the levels of components present therein, processing aids such as emulsifiers, and like considerations, but preferably ranges from about 5,000 cp to about 100,000 cp, and more preferably ranges from about 10,000 cp to about 60,000 cp. Viscosities of the compositions may be determined using a conventional viscometer.

PH

The pH of the compositions that are employed in the methods of the invention preferably ranges from about 2 to about 11, and more preferably ranges from about 5 to about 8, and may be adjusted using substances and methods known by those of skill in the art, such as acids (citric acid and the like) to decrease the pH or bases (sodium hydroxide and the like) to increase the pH.

Form of Compositions

The compositions that are employed in the methods of the invention may be present in any suitable or convenient state, including liquids, semi-solids and solids in, for example, a powder, crème, roll-on, aerosol, stick or other form. For example, the compositions may be in the form of a "leave-on" or "rinse-off" solution, lotion, cream, balsams, salve, oil, paste, ointment, gel, foam, solid, powder, antiperspirant, deodorant, aftershave, shaving lotion, shampoo, cream rinse or conditioner, hair-color product, hair-styling or finishing product (mouse, hair spray, hair gel, etc.), perming or body-wave product (hot wave, mild wave, cold wave, etc.), hair straightening preparation, hair-setting preparation, hair detangling product, other hair treatment product or the like. In order to achieve maximum effectiveness, it is preferred that the compositions be in, and applied as, a "leave-on" form. However, if the compositions are in a "rinse-off" form, it is preferred that the compositions not be rinsed off (or otherwise removed from the skin and/or hair) for a period of time that is sufficient for conditioning, which generally is at least about 4 minutes, and preferably is at least about 6 minutes, and more preferably is at least about 8 minutes, and still more preferably is at least about 10 minutes. Further, the compositions may be employed in a form of a skin-care product (skin cream, skin lotion, skin gel, skin foam, skin ointment, skin cleanser and the like), a cosmetic (base, foundation, concealer, loose powder, cake powder, rouge, etc.), a hair-care product, a veterinary product or the like. Liquid forms of the compositions include, but are not limited to, solutions, dispersions, emulsions and microemulsions (water-in-oil, oil-in-water, oil-in-water-in-oil, water-in-oil-in-water, and the like).

Preparation of Compositions

The compositions that are employed in the methods of the invention can be prepared using customary methods and equipment known by those of skill in the art for preparing skin and hair care products and cosmetics. For example, the Meadowlactone having a chemical structure set forth herein may be physically combined with a base to achieve the concentrations described herein by stirring together, or otherwise mixing or combining, the individual components. Preferably, sufficient agitation to achieve relative homogeneity is employed. Agitation may be achieved, for example, using a standard mixer, at a slow, moderate or even vigorous speed.

One formula for a skin cream composition that may be employed in the methods of the invention contains the components set forth below, and the concentrations thereof.

| Component | Weight Percent |
| --- | --- |
| Deionized water | 87.0-90.0% |
| Self-emulsifying wax N.F. (Fancor ® SEW-P) | 7.75% |
| Methylparaben/propylparaben (preservative) | 0.25% |
| Meadowlactone | 2.0% |

Other formulations for compositions that may be employed in the methods of the invention are provided in the Examples section set forth hereinbelow, and are commercially available from The Fanning Corporation (Chicago, Ill.).

Packaging

The compositions that are employed in the methods of the invention may be packaged in any suitable manner for packaging skin or hair care products or cosmetics, such as a plastic, metal or glass jar, bottle, tube, roll-on, compact case, cosmetic case or the like.

Quantity to be Administered and Application Rates

The compositions that are employed in the methods of the invention are preferably applied directly to the skin and/or hair of a mammal in an amount, and for a number of applications, that are effective for enhancing (improving) the morphology, tone, texture and/or appearance of the mammal's skin and/or hair.

The quantity of a composition to be administered to a mammal for each application depends upon the nature of the composition, the condition being treated and the area of the body involved, and may be determined by those of skill in the art using the information contained herein. The amount of a composition that will generally be effective for enhancing the morphology, tone, texture and/or appearance of the mammal's skin and/or hair may vary widely, depending upon a variety of factors, such as the type, age, sex, genetic predisposition and general health of the mammal, as well as the mammal's sun exposure, and may readily be determined by those of skill in the art. The amount of a composition that is applied to the skin or hair of a mammal per each application preferably ranges from about 1 to about 20 g or ml, and more preferably ranges from about 2 to about 12 g or ml, and still more preferably ranges from about 3 to about 8 g or ml, and even still more preferably ranges from about 4 to about 6 g or ml, with about 5 g or ml being most preferred. For example, about 5 g of the composition may be applied to the skin and/or hair of a mammal from a suitable container or applicator and spread over, or rubbed into, the skin or hair using the hands or fingers or a suitable application or other device.

The number of applications of a composition to the skin and/or hair of a mammal that will generally be effective for producing an improvement in the morphology, tone, texture and/or appearance of the mammal's skin and/or hair, and the period of time during which such applications are made, may vary widely, depending upon a variety of factors, such as the concentration of the Meadowlactone in the composition, the amount of the composition that is applied to the mammal's skin and/or hair, the condition of the mammal's skin and/or hair, the amount of the mammal's sun exposure and the type, age, sex, genetic predisposition and general health of the mammal, and may readily be determined by those of skill in the art. Typically, at least about three applications of the composition to the skin and/or hair of the mammal (three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty and so forth applications) continuously over a period of at least about one day or week, or a series of days or weeks (one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty and so forth days or one, two, three, four, five, six, seven, eight, nine, ten, eleven, twelve, and so forth weeks) will be effective for improving the morphology, tone, texture and/or appearance of the mammal's skin and/or hair. The compositions may, for example, be applied as a cream, lotion, ointment or other convenient form as frequently as once per hour and as infrequently as once per day.

Generally, the higher the number of applications of the composition to the skin and/or hair of a mammal within a period of time, the greater an improvement will be observed or otherwise detected in the morphology, tone, texture and/or appearance of the skin and/or hair, and the less time will be required for achieving such results. Although there generally is no limit to the number of applications of the composition that can be applied to the skin and/or hair of a mammal, above a certain number of applications, no further improvement in the morphology, tone, texture and/or appearance of the skin and/or hair may be observed or otherwise detected.

The table below shows examples of some of the skin and hair application protocols that can be employed with the Meadowlactone employed in the present invention at concentrations that are described herein.

Examples of Application Protocols

| Number of Applications | Number of Days |
|---|---|
| 1 time each day | 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 and so forth |
| 2 times each day | 1 and ½, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 and so forth |
| 3 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 4 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 5 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 6 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 7 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 8 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 9 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 10 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 11 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 12 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 13 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 14 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 15 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 16 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 17 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 18 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 19 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 20 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 21 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 22 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |
| 23 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |

| Number of Applications | Number of Days |
|---|---|
| 24 times each day | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and so forth |

It is preferable, but not necessary, that the various applications of the Meadowlactone that are applied each day be equally spaced with a 24-hour period. For example, it is preferable that two applications that are to be applied in one day are applied approximately 12 hours apart. It is preferable that three applications that are to be applied in one day are applied approximately 8 hours apart. It is preferable that four applications that are to be applied in one day are applied approximately 6 hours apart. It is preferable that five applications that are to be applied in one day are applied approximately 4.8 hours apart, and so forth. It is also preferable that days not be missed when a series of applications are to be made over a specified number of days.

As an example, after a composition containing about 4 weight percent of the Meadowlactone is applied one time per day to the skin and/or hair of a mammal that requires, or could benefit from, skin and/or hair treatment, an improvement in the morphology, tone, texture and/or appearance of the skin and/or hair of the mammal will typically be observed or otherwise detected after a period of from about 4 to about 9 days. If the same composition is applied two times per day to the mammal's skin and/or hair, an improvement in the morphology, tone, texture and/or appearance of the skin and/or hair of the mammal will typically be observed or otherwise detected after a period of from about 4 to about 8 days. If the same composition is applied three times per day to the mammal's skin and/or hair, an improvement in the morphology, tone, texture and/or appearance of the skin and/or hair of the mammal will typically be observed or otherwise detected after a period of from about 4 to about 7 days. If the same composition is applied four times per day to the mammal's skin and/or hair, an improvement in the morphology, tone, texture and/or appearance of the skin and/or hair of the mammal will typically be observed or otherwise detected after a period of from about 4 to about 6 days. If the same composition is applied five times per day to the mammal's skin and/or hair, an improvement in the morphology, tone, texture and/or appearance of the skin and/or hair of the mammal will typically be observed or otherwise detected after a period of from about 4 to about 5 days.

As another example, if a composition containing about 6 weight percent of the Meadowlactone is applied one time per day to the skin and/or hair of the mammal, an improvement in the morphology, tone, texture and/or appearance of the skin and/or hair of the mammal will typically be observed or otherwise detected after a period of from about 3 to about 8 days. If the same composition is applied two times per day to the mammal's skin and/or hair, an improvement in the morphology, tone, texture and/or appearance of the skin and/or hair of the mammal will typically be observed or otherwise detected after a period of from about 3 to about 7 days. If the same composition is applied three times per day to the mammal's skin and/or hair, an improvement in the morphology, tone, texture and/or appearance of the skin and/or hair of the mammal will typically be observed or otherwise detected after a period of from about 3 to about 6 days. If the same composition is applied four times per day to the mammal's skin and/or hair, an improvement in the morphology, tone, texture and/or appearance of the skin and/or hair of the mammal will typically be observed or otherwise detected after a period of from about 3 to about 5 days. If the same composition is applied five times per day to the mammal's skin and/or hair, an improvement in the morphology, tone, texture and/or appearance of the skin and/or hair of the mammal will typically be observed or otherwise detected after a period of from about 3 to about 4 days.

As yet another example, if a composition containing about 9 weight percent of the Meadowlactone is applied one time per day to the skin and/or hair of the mammal, an improvement in the morphology, tone, texture and/or appearance of the skin and/or hair of the mammal will typically be observed or otherwise detected after a period of from about 2 to about 7 days. If the same composition is applied two times per day to the mammal's skin and/or hair, an improvement in the morphology, tone, texture and/or appearance of the skin and/or hair of the mammal will typically be observed or otherwise detected after a period of from about 2 to about 6 days. If the same composition is applied three times per day to the mammal's skin and/or hair, an improvement in the morphology, tone, texture and/or appearance of the skin and/or hair of the mammal will typically be observed or otherwise detected after a period of from about 2 to about 5 days. If the same composition is applied four times per day to the mammal's skin and/or hair, an improvement in the morphology, tone, texture and/or appearance of the skin and/or hair of the mammal will typically be observed or otherwise detected after a period of from about 2 to about 4 days. If the same composition is applied five times per day to the mammal's skin and/or hair, an improvement in the morphology, tone, texture and/or appearance of the skin and/or hair of the mammal will typically be observed or otherwise detected after a period of from about 2 to about 3 days.

As another example, if a composition containing about 12 weight percent of the Meadowlactone is applied one time per day to the skin and/or hair of the mammal, an improvement in the morphology, tone, texture and/or appearance of the skin and/or hair of the mammal will typically be observed or otherwise detected after a period of from about 1 to about 6 days. If the same composition is applied two times per day to the mammal's skin and/or hair, an improvement in the morphology, tone, texture and/or appearance of the skin and/or hair of the mammal will typically be observed or otherwise detected after a period of from about 1 to about 5 days. If the same composition is applied three times per day to the mammal's skin and/or hair, an improvement in the morphology, tone, texture and/or appearance of the skin and/or hair of the mammal will typically be observed or otherwise detected after a period of from about 1 to about 4 days. If the same composition is applied four times per day to the mammal's skin and/or hair, an improvement in the morphology, tone, texture and/or appearance of the skin and/or hair of the mammal will typically be observed or otherwise detected after a period of from about 1 to about 3 days. If the same composition is applied five times per day to the mammal's skin and/or hair, an improvement in the morphology, tone, texture and/or appearance of the skin and/or hair of the mammal will typically be observed or otherwise detected after a period of from about 1 to about 2 days.

As still another example, if a composition containing about 15 weight percent of the Meadowlactone is applied one time per day to the skin and/or hair of the mammal, an improvement in the morphology, tone, texture and/or appearance of the skin and/or hair of the mammal will typically be observed or otherwise detected after a period of from about 0.5 to about 5 days. If the same composition is applied two times per day to the mammal's skin and/or hair, an improvement in the morphology, tone, texture and/or appearance of the skin and/or hair of the mammal will typically be observed or otherwise detected after a period of from about 0.5 to about 4 days. If the same composition is applied three times per day to the mammal's skin and/or hair, an improvement in the morphology, tone, texture and/or appearance of the skin and/or hair of the mammal will typically be observed or otherwise detected after a period of from about 0.5 to about 3 days. If the same composition is applied four times per day to the mammal's skin and/or hair, an improvement in the morphology, tone, texture and/or appearance of the skin and/or hair of the mammal will typically be observed or otherwise detected after a period of from about 0.5 to about 2 days. If the same composition is applied five times per day to the mammal's skin and/or hair, an improvement in the morphology, tone, texture and/or appearance of the skin and/or hair of the mammal will typically be observed or otherwise detected after a period of from about 0.5 to about 1 day.

It is preferable that at least 15 applications of the composition are applied to the skin and/or hair of a mammal over a period of about 5 days, for example, 3 applications of the composition to the skin and/or hair per day for a period of 5 days. It is more preferable that at least 60 applications of the composition are applied to the skin and/or hair of a mammal over a period of about 15 days, for example, 4 applications of the composition to the skin and/or hair per day for a period of 15 days. It is still more preferable that at least 120 applications of the composition are applied to the skin and/or hair of a mammal over a period of about 30 days, for example, 4 applications of the composition to the skin and/or hair per day for a period of 30 days.

Sources of Ingredients

All of the ingredients, materials and equipment employed in the examples, and generally employed in the methods of the invention, are commercially available from sources known by those of skill in the art, such as The Fanning Corporation (Chicago, Ill.), Botagenics, Inc. (Northridge, Calif.), Base Formula, Ltd. (Melton Mowbray, England), Well Naturally Products, Ltd. (Blaine, Wash.), Essential Wholesale (Clackamas, Oreg.), Urist Cosmetics, Inc. (Richmond, Calif.), Sciencelab.com, Inc. (Houston, Tex.), Fluka Chemical and Biochemical Co. (Ronkonkoma, N.Y.), Sony North America (New York, N.Y.), NOVA Technology Corporation (Portsmouth, N.H.) and ServoMed (Sweden).

The following examples describe and illustrate the methods of the present invention. These examples are intended to be merely illustrative of the present invention, and not limiting thereof in either scope of spirit. Those of skill in the art will readily understand that variations of certain of the conditions and/or steps employed in the procedures described in the examples can be employed.

EXAMPLE 1

Preparation of Meadowlactone

The Meadowlactone that is employed in the methods of the invention, the structure of which is set forth hereinbelow, was synthesized from the meadowfoam seed oil fatty acids that are set forth below, which are naturally present in meadowfoam seed oil, and scaled-up using a cyclical ring closure to $\Delta^6$ reaction process (to form a lactone) followed by a series of high vacuum distillations (to purify the material). Unsaturation at the $\Delta^{5-6}$ and $\Delta^{13,14}$ locations enables the synthesis of the Meadowlactone.

| Meadowfoam Seed Oil Fatty Acids | Weight Percent of Total Fatty Acids Present in Meadowfoam Seed Oil |
|---|---|
| $CH_3—(CH_2)_{13}—(CH)_2—(CH_2)_3—COOH$ $\Delta^5$ 20:1 | 63% |
| $CH_3—(CH_2)_{15}—(CH)_2—(CH_2)_3—COOH$ $\Delta^5$ 22:1 | 4% |
| $CH_3—(CH_2)_7—(CH)_2—(CH_2)_{11}—COOH$ $\Delta^{13}$ 22:1 | 12% |
| $CH_3—(CH_2)_7—(CH)_2—(CH_2)_6—(CH)_2—(CH_2)_3—COOH$ $\Delta^{5,13}$ 22:1 | 17% |

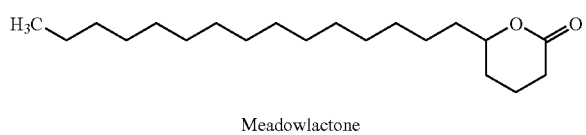

Meadowlactone

Analytical results indicated a high level of purity and extended stability for the Meadowlactone. The purified Meadowlactone was identified and subsequently quantified by infrared spectroscopy and HPLC coupled with an evaporative light-scattering detector.

This Meadowlactone is commercially available from The Fanning Corporation (Chicago, Ill.).

EXAMPLE 2

Preparation of Skin Cream Containing Meadowlactone

A skin cream composition including the Meadowlactone prepared in Example 1 was prepared using a skin cream base. The composition contained the components set forth below, and the concentrations thereof.

| Component | Weight Percent |
|---|---|
| Deionized water | 87.0-90.0% |
| Self-emulsifying wax N.F. (Fancor ® SEW-P) | 7.75% |
| Methylparaben/propylparaben (preservative) | 0.25% |
| Meadowlactone | 2.0% |

The composition was prepared by separately heating to 80 degrees centigrade: (a) the Self-emulsifying wax N.F. and the Meadowlactone; and (b) the water containing the preservatives. Then, the oil phase (melted wax) was slowly added to the water phase with vigorous mixing, with a cooling of the mixture commencing while mixing. A cream began to set up as the mixture cooled. The mixture was cooled until it reached about 40 degrees centigrade. Mixing was discontinued and the final skin cream product was formed by standing at room temperature.

EXAMPLE 3

Physical Chemistry Studies of Meadowlactone

Initial use trials of skin creams containing the Meadowlactone described herein indicated that the compound provided very effective skin "moisturization," which appeared to last for a longer period of time than would be expected from simple topical skin cream applications. In an attempt to better understand the biochemical mechanisms underlying the ability of this Meadowlactone to have such a pronounced effect upon epidermal tissue, a series of physical chemistry experiments were conducted to examine the structural configuration of the Meadowlactone under conditions simulating those likely to occur in tissue. Solubility of the Meadowlactone as a function of pH was determined in aqueous systems.

In these experiments, 2 weight percent of Meadowlactone was mixed with water at room temperature. The pH of this mixture was varied, starting at an acidic pH and terminating at an alkaline pH. The clarity of the mixture was observed, and the mixture was photographed, at different pH levels (varying by one pH unit at a time).

The results of these experiments, and their implication with respect to "moisturizing or conditioning" tissue, are shown in FIG. 1, which is a diagram of the dynamic equilibrium between water-soluble and oil-soluble forms of the Meadowlactone, and the Meadowlactone bioactivity, at an alkaline, neutral and acid pH.

The results of these experiments show that the Meadowlactone is an amphoteric compound having isomeric structures (FIG. 1) that have an ability to shift between oil and water solubility as a function of pH. At an acidic pH, the Meadowlactone exists as a closed ring structure (bottom structure in FIG. 1). As the pH is raised, however, its ring structure opens, and a resulting intermediate compound (middle structure in FIG. 1) generally becomes quickly hydrated to form a 5-hydroxy fatty acid (top structure in FIG. 1). This transition between isomeric structures is physiologically significant because the Meadowlactone is oil soluble and the 5-hydroxy fatty acid is water soluble.

From the results of these experiments, it was concluded that, at the pH reported for human skin (from about 4.5 to about 5.5), both the Meadowlactone and the 5-hydroxy fatty acid exist together in equilibrium. It was also concluded that, within epidermal tissue that has had the Meadowlactone applied thereto, both oil soluble and water soluble forms of the compound are present in the skin, which facilitates a maintenance of a physiologically correct balance of oil and water within the treated epidermal tissue.

EXAMPLE 4

Applications of Meadowlactone and Control Skin Creams to Human Skin

In these topical application experiments, a simple cream base containing no conditioning or active agents other than the test material (Meadowlactone skin cream prepared in Example 2, but containing varying quantities of Meadowlactone), and appropriate control skin creams (skin cream base alone or skin cream base plus water or petrolatum) were applied to the skin of human beings in varying quantities and at varying application rates.

Subjects and Application Protocols

The panel of subjects used for these studies were both male and female ranging from twenty to forty one years of age. Initial applications of the Meadowlactone skin cream composition and skin cream controls, and instructions for subsequent applications, were supervised by a professional aesthetician. A variety of application procedures were employed in an attempt to reflect actual market usage of these types of products, as well as to determine the extent to which observed results were a function of duration and/or frequency of use. The application protocols (frequency and duration of use), and concentration of test material used, varied as is discussed below. Each member of the panel applied Meadowestolide skin cream and/or an appropriate control, to their face, hands or forearms.

Although application studies were performed on approximately 20 subjects, only three of the subjects are discussed herein because the results for these two subjects were typical of the results obtained for all of the subjects.

Image Capture and Processing Instrumentation The following image capture and processing instrumentation were employed in these experiments:

(1) a Sony Cyber-Shot digital still camera equipped with an X1.4 Teleconversion lens (VCL-1452H) (Sony North America, New York, N.Y.); and (2) a "Micro-Topological Epidermal Imaging" (MTEI) instrument using a portable high magnification fiber optic microscope (to achieve a higher magnification in vivo visualization of skin tissue).

External lighting sources were employed to facilitate the visualization of epidermal surface topography. In some instances, optical shadow casting techniques were used to better define surface topology.

Experiments and Results

Figure 2:
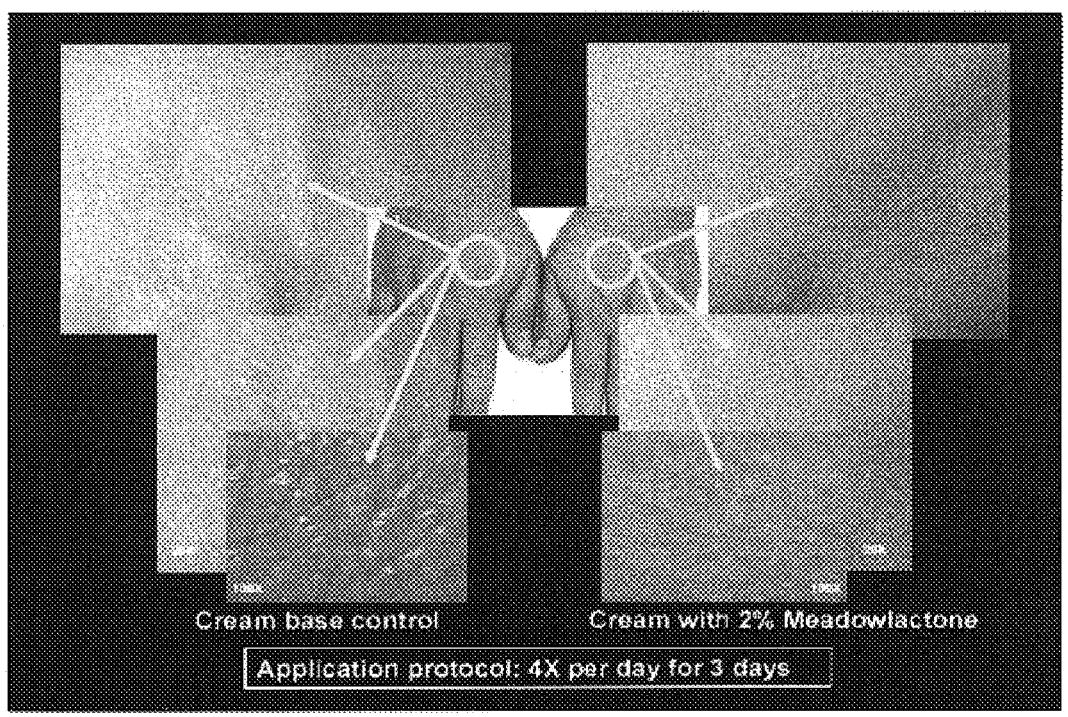
FIG. 2 is a series of seven photographs produced using Micro-Topological Epidermal Imaging (MTEI) and resulting from experiments that are described in Example 4. These photographs show a 41-year old female subject's left hand that was treated with a Meadowlactone skin cream containing 2% of Meadowlactone (as the only active ingredient), and the same subject's right hand that was treated with a control skin cream (the same skin cream, but formulated with 2% of water in place of the Meadowlactone), the application rate for each hand being four times per day for a period of three days. These photographs also show portions of the treated skin from the left hand without magnification, with 20× magnification and with 100× magnification (right series of photographs) and portions of treated skin from the right hand without magnification, with 20× magnification and with 100× magnification (left series of photographs).

In a first experiment, a 41-year old female subject applied the Meadowlactone skin cream containing 2% of Meadowlactone (as the only active ingredient) to the left hand and a control skin cream (the same skin cream, but formulated with 2% water in place of the Meadowlactone) to the right hand, both at an application rate of four times per day for a period of three days. The results of this experiment are shown in FIG. 2 (seven photographs of the right and left hand without magnification, with 20× magnification and with 100× magnification). The middle photograph shows the subject's left hand (to the right) and right hand (to the left) after treatment. The right series of photographs show the subject's left hand without magnification, with 20× magnification and with 100× magnification after treatment. The left series of photographs show the subject's right hand without magnification, with 20× magnification and with 100× magnification after treatment. FIG. 2 clearly shows that the subject's left hand (treated with Meadowlactone skin cream) has a significant improvement in the surface topology of the skin (visually observable reduced irregularities and wrinkling) in comparison with the right hand (treated with the control skin cream).

Figure 3:
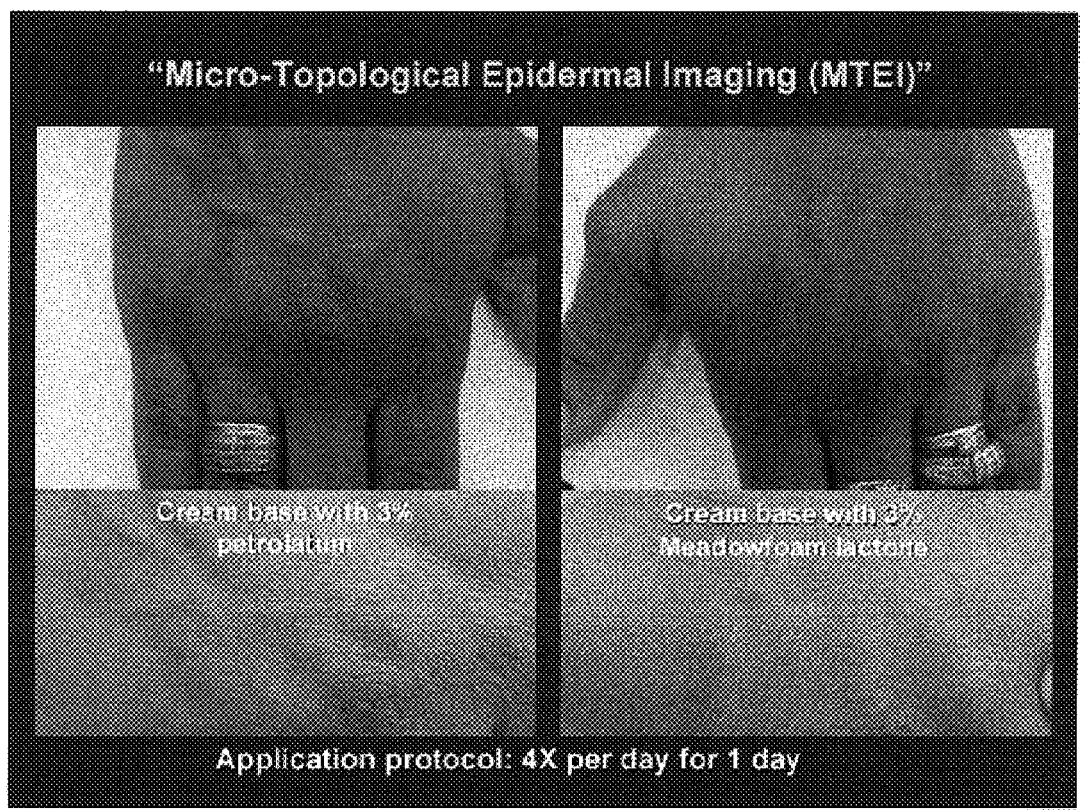
FIG. 3 is a series of four photographs produced using Micro-Topological Epidermal Imaging (MTEI) and resulting from experiments that are described in Example 4. These photographs show a 39-year old female subject's left hand that was treated with a Meadowlactone skin cream containing 3% of Meadowlactone (as the only active ingredient), and the same subject's right hand that was treated with a control skin cream (the same skin cream, but formulated with 3% petrolatum in place of the Meadowlactone), the application rate for each hand being four times per day for a period of one day. These photographs also show a portion of treated skin from the left hand (right series of photographs), and a portion of treated skin from the right hand (left series of photographs), without magnification.

In a second experiment, a 39-year old female subject applied the Meadowlactone skin cream containing 3% of Meadowlactone (as the only active ingredient) to the left hand and a control skin cream (the same skin cream, but formulated with 3% petrolatum in place of the Meadowlactone) to the right hand, each at an application rate of four times per day for a period of one day. The results of this experiment are shown in FIG. 3, which contains Micro-Topological Epidermal Imaging photographs of the left hand, and of a portion of treated skin from the left hand (right series of photographs), and of the right hand, and of a portion of treated skin from the right hand (left series of photographs), without magnification after treatment. FIG. 3 clearly shows that the subject's left hand (treated with Meadowlactone skin cream) has a significant improvement in the surface topology of the skin (visually observable reduced irregularities and wrinkling) in comparison with the right hand (treated with the control skin cream).

"Dry elbows" is a common complaint by human beings and, thus, provides a desirable test system for moisturization and conditioning. In a third experiment, a 40-year old female subject who had previously experienced difficulties in keeping her skin "moisturized" applied the Meadowlactone skin cream containing 3% of Meadowlactone (as the only active ingredient) to one elbow and a control skin cream (the same skin cream, but formulated with 3% petrolatum in place of the Meadowlactone) to the other elbow, both at an application rate of four times per day for a period of one and one half days (six applications total of each composition).

Figure 4:
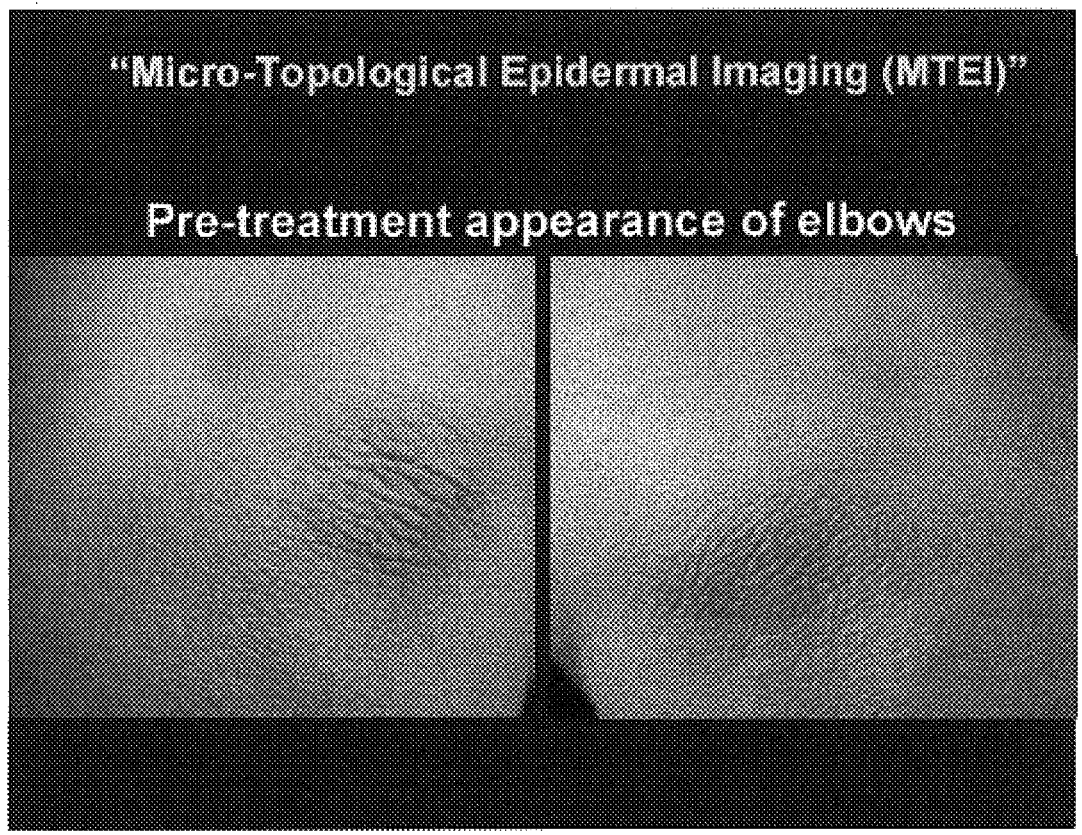
FIG. 4 is a series of two photographs produced using Micro-Topological Epidermal Imaging (MTEI) and resulting from experiments that are described in Example 4. These photographs show both of the elbows of a 40-year old female subject prior to any treatment (a pre-treatment appearance of both of the elbows).

FIG. 4 contains Micro-Topological Epidermal Imaging photographs of both of the subject's elbows prior to any treatment (a pre-treatment appearance of both elbows). In these photographs, the subject's elbows both appear to be dry and wrinkled.

Figure 5:
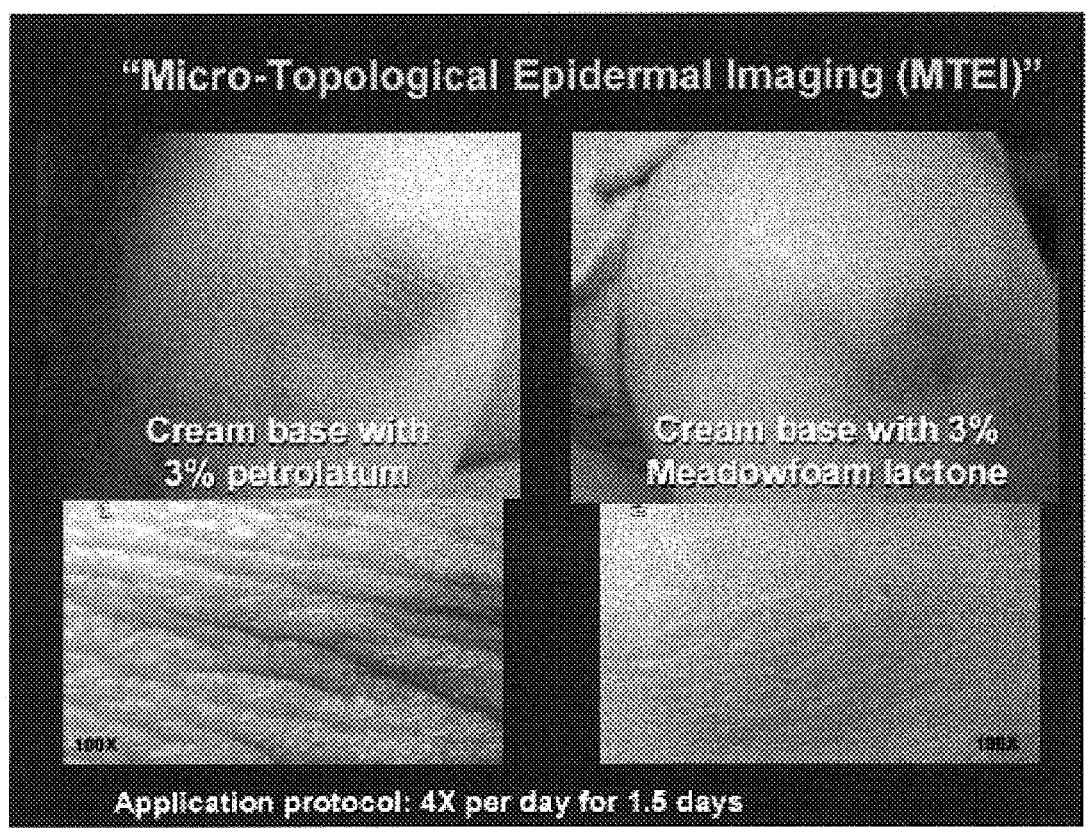
FIG. 5 is a series of four photographs produced using Micro-Topological Epidermal Imaging (MTEI) and resulting from experiments that are described in Example 4. These photographs show the same elbows that are described above in connection with FIG. 4, with the exception that the elbows were photographed after treatment (six applications over a period of 1.5 days for each elbow) with either a Meadowlactone skin cream (containing 3 weight percent Meadowlactone as the only active ingredient—upper and lower right photographs) or with a control skin cream (the same skin cream, but containing 3 weight percent of petrolatum in place of the Meadowlactone—upper and lower left photographs), both without magnification and with a 100× magnification. The upper left photograph shows the elbow that was treated with the control skin cream without magnification. The lower left photograph shows the same elbow (after treatment with the control skin cream) at a 100× magnification. The upper right photograph shows the elbow that was treated with the Meadowlactone skin cream without magnification. The lower right photograph shows the same elbow (after treatment with the Meadowlactone skin cream) at a 100× magnification.

FIG. 5 contains Micro-Topological Epidermal Imaging photographs of the same elbows following treatment (a post-treatment appearance of both elbows), and both without magnification and with a 100× magnification. The upper left photograph shows the elbow that was treated with the control skin cream without magnification. The lower left photograph shows the same elbow (after treatment with the control skin cream) at a 100× magnification. In both of these photographs, the subject's elbow appears to be dry and wrinkled. The upper right photograph shows the elbow that was treated with the cream base containing Meadowlactone without magnification. The lower right photograph shows the same elbow (after treatment with the Meadowlactone skin cream) at a 100× magnification. In both of these photographs (upper right and lower right), the subject's elbow appears to be significantly less dry and wrinkled in comparison with the elbow that was treated with the control skin cream (upper left and lower left photographs), and in comparison with both elbows prior to any treatment (FIG. 4). FIG. 5 clearly shows that the subject's elbow (treated with the Meadowlactone skin cream) has a significant improvement in the tone of the skin (visually observable reduced irregularities, wrinkling and dryness) following the applications of the Meadowlactone skin cream in comparison with the elbow (treated with the control skin cream), and in comparison with both elbows prior to any treatment. The benefits provided by the Meadowlactone skin cream appear to be the most visually apparent at the higher 100× magnification.

EXAMPLE 5

Muscle Relaxant Skin Formulation

| Ingredient | Weight % | INCI Name | Function |
|---|---|---|---|
| 1. Deionized Water | q.s. | Water | Diluent |
| 2. Methylparaben, Propylparaben | 0.25 | Methylparaben, Propylparaben | Preservative |
| 3. Fanwax ™ Sew-P | 5.50 | Emulsifying wax NF | Emulsifier/ Thickener |
| 4. Fancor ® Lanolin USP | 5.55 | Lanolin | Emollient/ Conditioner |
| 5. White Petrolatum | 3.50 | Petrolatum | Conditioner/ Protectant |
| 6. Mineral Oil | 2.00 | Mineral Oil | Emollient/ Lubrication |
| 7. Meadowlactone | 2.00 | Meadowfoam Delta Lactone | Active Agent |
| 8. Menthol | 0.55 | Menthol | Cooling Agent/ Medicinal |
| 9. Eucalyptus Oil | 0.50 | Eucalyptus | Cooling Agent/ Medicinal |
| 10. Camphor | 1.00 | Camphor | Cooling Agent/ Medicinal |
| 11. Peppermint Oil | 1.00 | Peppermint | Calming Agent/ Medicinal |
| 12. Phenoxyethol | 0.40 | Phenoxyethanol | Preservative |
| 13. *Symphytum Officinale* Extract *Plantago Ovata* Seed Extract *Sambucus Nigra* Flower Extract *Equisetum Arvense* Extract *Calendula Officinalis* Flower Extract *Salvia Officinalis* (Sage) Leaf Extract *Geramium Maclatum* Extract *Panax Ginseng* Root Extract Honey Extract | 0.25 | *Symphytum Officinale* Extract *Plantago Ovata* Seed Extract *Sambucus Nigra* Flower Extract *Equisetum Arvense* Extract *Calendula Officinalis* Flower Extract *Salvia Officinalis* (Sage) Leaf Extract *Geramium Maclatum* Extract *Panax Ginseng* Root Extract Honey Extract | Herbal/ Botanicals |

Preparative Procedure:

Ingredients 1. and 2. were heated to 75° C. in a main vessel. Separately, ingredients 3., 4., 5., 6. and 7. were heated to 75° C., added to the water phase and mixed strongly for 15 minutes. The mixture was then slowly agitated and cooled to 55° C. Ingredients 8., 9., 10. and 11 were added, with mixing continued until homogenous. The mixture was cooled to 30° C. Ingredients 12. and 13 were added, and cooling was continued until the mixture reached room temperature.

Ingredients 3., 4. and 7. are commercially available from The Fanning Corporation (Chicago, Ill.).

Characteristics:
pH: 4.00-5.50
Viscosity: 12,000-16,000 cps @ 25° C.
Appearance: White to off white thick cream.

EXAMPLE 6

Hand and Body Moisturizing Lotion

| Ingredient | Weight % | INCI Name | Function |
|---|---|---|---|
| 1. Deionized Water | 71.10 | Water | Diluent |
| 2. Glycerin 99% | 3.00 | Glycerin | Humectant |
| 3. Mineral Oil | 8.00 | Mineral Oil | Emollient |
| 4. Fanwax ® SEW-P | 3.00 | Emulsifying Wax NF | Emulsifier |
| 5. Cetearyl Alcohol | 1.50 | Cetearyl Alcohol | Thickener |
| 6. Meadowlactone | 2.00 | Meadowfoam Delta Lactone | Active Agent |
| 7. Phenoxyethanol, Methylparaben, Propylparaben, Butylparaben, and Ethylparaben | 1.00 | Phenoxyethanol, Methylparaben, Propylparaben, Butylparaben, and Ethylparaben | Preservative |
| 8. Fancorsil ® HA Super | 10.00 | Glyceryl Polyacrylate Dimethicone, Cyclomethicone | Emulsifier/Thickener |
| 9. DMDM Hydantoin | 0.40 | DMDM Hydantoin | Preservative |

Preparative Procedure:

Ingredients 1. and 2. are heated to 75° C. in a main vessel. Separately, ingredients 3., 4., 5. and 6. are heated to 80° C. and added to the water phase, and mixed well for 15 minutes. Using slow agitation, the mixture is cooled to 50° C. Ingredients 7. and 8. are added and mixed until homogenous. Ingredient 9. is added and cooling is continued until the mixture reaches 30° C.

Ingredients 4., 6. and 8. are commercially available from The Fanning Corporation (Chicago, Ill.).

Characteristics:
pH: 6-7;
Viscosity: 3,000-5,000 cps.

EXAMPLE 7

Hand Moisturizing Cream

| Ingredient | Weight % | INCI Name | Function |
|---|---|---|---|
| 1. Deionized Water | 70.10 | Water | Diluent |
| 2. Glycerin 99% | 3.00 | Glycerin | Humectant |
| 3. Mineral Oil | 5.00 | Mineral Oil | Emollient |
| 4. Fanwax ® Sew-P | 3.00 | Emulsifying Wax, NF | Emulsifier |
| 5. Fancol ® VB | 5.00 | Limnanthes Alba (Meadowfoam) Seed oil, Butyrospermum Parkii (Shea Butter) Extract | Conditioner |
| 6. Cetearyl Alcohol | 1.50 | Cetearyl Alcohol | Thickener |
| 7. Meadowlactone | 3.00 | Meadowfoam Delta Lactone | Active Agent |
| 8. Phenoxyethanol, Methylparaben, Ethylparaben, Butylparaben, and Propylparaben | 1.00 | Phenoxyethanol, Methylparaben, Ethylparaben, Butylparaben, and Propylparaben | Preservative |
| 9. Fancorsil ® HA Super | 8.00 | Glyceryl Polyacrylate | Emulsifier/Thickener |
| 10. DMDM Hydantoin | 0.40 | DMDM Hydantoin | Preservative |

Preparative Procedure:

Ingredients 1. and 2. were heated to 75° C. in a main vessel. Separately, ingredients 3., 4., 5. and 6 were heated to 80° C. and added to the water phase, and then mixed well for 15 minutes. Using slow agitation, the mixture was cooled to 50° C. Ingredients 7. and 8. were added and mixed until homogenous. Ingredients 9. and 10. were added and mixed, with cooling continued to 30° C.

Ingredients 4., 5., 7. and 9. are commercially available from The Fanning Corporation (Chicago, Ill.).

Characteristics:
pH: 6-7
Viscosity: 5,000-8,000 cps

EXAMPLE 8

Hand Moisturizing Cream

| Ingredient | Weight % | INCI Name | Function |
|---|---|---|---|
| 1. Deionized Water | 75.35 | Water | Diluent |
| 2. Glycerin 99% | 3.00 | Glycerin | Humectant |
| 3. Mineral Oil | 5.00 | Mineral Oil | Emollient |
| 4. Fancor ® Uni-Embase | 3.00 | Cetearyl Alcohol, Dimethicone PEG-8 Meadowfoamate, Meadowfoam Amidopropyldimethyl Betaine | Emulsifier |
| 5. Fancol ® VB | 5.00 | Meadowfoam (Limnanthes Alba) Seed oil, Shea Butter (Butyrospermum Parkii) Extract | Conditioner |
| 6. Cetearyl Alcohol | 1.50 | Cetearyl Alcohol | Thickener |
| 7. Meadowlactone | 2.00 | Meadowfoam Delta Lactone | Active Agent |
| 8. Phenoxyethanol, Methylparaben, Butylparaben, Ethylparaben, and Propylparaben | 0.75 | Phenoxyethanol, Methylparaben, Butylparaben, Ethylparaben, and Propylparaben | Preservative |

-continued

Hand Moisturizing Cream

| Ingredient | Weight % | INCI Name | Function |
|---|---|---|---|
| 9. Fancorsil ® HA Super | 4.00 | Glyceryl Polyacrylate | Emulsifier/Thickener |
| 10. DMDM Hydantoin | 0.40 | DMDM Hydantoin | Preservative |

Preparative Procedure:

Ingredients 1. and 2. were heated to 75° C. in a main vessel. Separately, ingredients 3., 4., 5. and 6. were heated to 80° C. and added to the water phase, and then mixed well for 15 minutes. Using slow agitation, the mixture was cooled to 50° C. Ingredients 7. and 8. were added and mixed until homogenous. Ingredients 9. and 10. were added and mixed, with cooling continued to 30° C.

Ingredients 4., 5., 7. and 9. are commercially available from The Fanning Corporation (Chicago, Ill.).

Characteristics:
pH: 4.0-5.0
Viscosity: 10,000-18,000 cps

EXAMPLE 9

Hand/Skin Cream Moisturizing Conditioner

| Ingredient | Weight % | INCI Name | Function |
|---|---|---|---|
| 1. Deionized Water | 85.35 | Water | Diluent |
| 2. Glycerin 99% | 3.00 | Glycerin | Humectant |
| 3. Methylparaben, Propylparaben | 0.25 | Methylparaben, Propylparaben | Preservative |
| 4. Fancorgel ® A | 4.00 | Sodium Acrylates Copolymer, Dimethiconol Meadowfoamate, Mineral Oil, PPG-1 Trideceth-6 | Emulsifier/Thickener/Conditioner |
| 5. Fancol ® VB | 5.00 | *Limnanthes Alba* (Meadowfoam) Seed Oil, *Butyrospermum Parkii* (Shea Butter) Extract | Conditioner |
| 6. Meadowlactone | 2.00 | Meadowfoam Delta Lactone | Active Agent |
| 7. DMDM Hydantoin | 0.40 | DMDM Hydantoin | Preservative |

Preparative Procedure:

Ingredients 1., 2. and 3. were heated to 45° C. in a main vessel. Once uniform, ingredient 4. was added, and the ingredients were mixed well until the mixture thickened. Ingredients 5., 6. and 7. were added and mixed with the mixture until homogenous. The resulting mixture was cooled to 30° C.

Ingredients 4., 5. and 6. are commercially available from The Fanning Corporation (Chicago, Ill.).

Characteristics:
pH: 6-7
Viscosity: 15,000-25,000 cps

EXAMPLE 10

Leave-On Bi-Layer Sunscreen

| Ingredient | Weight % | INCI Name | Function |
|---|---|---|---|
| 1. Deionized Water | q.s | Water | Diluent |
| 2. Methylparaben, Propylparaben | 0.25 | Methylparaben, Propylparaben | Preservative |
| 3. FD&C Red 33 | 0.003 | Red 33 | Color |
| 4. Fancol ® IH-CG | 25.0 | Isohexadecane | Emollient |
| 5. Isopropyl Myristate | 14.00 | Isopropyl Myristate | Conditioner |
| 6. Meadowlactone | 3.00 | Meadowfoam Delta Lactone | Active Agent |
| 7. D&C Green #6 | 0.0006 | Green 6 | Color |
| 8. Octyl Methoxycinnamate | 7.50 | Octyl Methoxycinnamate | Sunscreen Agent |
| 9. Tocopheryl Acetate | 0.05 | Tocopheryl Acetate | Antioxidant |

Preparative Procedure:

In a main tank, ingredients 2. and 3. were mixed in ingredient 1. until uniform. Once clear, the mixture was set aside. In a separate vessel, ingredients 4., 5., 6., 7., 8. and 9. were combined, and were mixed until uniform and homogeneous. When both tanks (phases) were ready, they were put into a packaging container in a ratio of 50:50.

Ingredients 4. and 6. are commercially available from The Fanning Corporation (Chicago, Ill.).

Appearance: Clear Distinct Bi-layers of Light Green and Red Liquids

EXAMPLE 11

Moisturizing Skin Cream

| Ingredient | Weight % | INCI Name | Function |
|---|---|---|---|
| 1. D.I. Water | q.s. | Water | Diluent |
| 2. Methylparaben, Propylparaben | 0.25 | Methylparaben, Propylparaben | Preservative |
| 3. Glycerin, 99% | 3.00 | Glycerin | Humectant |
| 4. Fancor ® Uni-Embase | 5.00 | Cetearyl Alcohol, Polysorbate 65, Dimethicone PEG-8 Meadowfoamate, Meadowfoam Amidopropyldimethyl Betaine | Emulsifier/Thickener |
| 5. Cetearyl Alcohol | 0.50 | Cetearyl Alcohol | Thickener |
| 6. Mineral Oil, (70VS) | 10.00 | Mineral Oil | Emollient |
| 7. Meadowlactone | 2.00 | Meadowfoam Delta Lactone | Active Agent |
| 8. DMDM Hydantoin | 0.40 | DMDM Hydantoin | Preservative |
| 9. Matricaria Extract | 0.15 | Matricaria Extract | Botanical |

Preparative Procedure:

The ingredients were heated separately to 80° C., and then combined and mixed well with good shear. The mixture was dearated and cooled to 55° C. with continued agitation.

Ingredients 4. and 7. are commercially available from The Fanning Corporation (Chicago, Ill.).

Appearance/Characteristics:
White cream
pH: 4.25-5.25
Viscosity: 10,000-15,000 cps

EXAMPLE 12

Skin Moisturizing Lotion

| Ingredient | Weight % | INCI Name | Function |
|---|---|---|---|
| 1. Deionized Water | q.s. | Water | Diluent |
| 2. Propylene Glycol, USP | 5.00 | Propylene Glycol | Humectant |
| 3. Methylparaben | 0.25 | Methylparaben | Preservative |
| 4. Mineral Oil | 7.50 | Mineral Oil, Propylparaben | Emollient |
| 5. Fancor ® Uni-Embase | 4.50 | Cetearyl Alcohol, Polysorbate 65, Dimethicone PEG-8 Meadowfoamate, Meadowfoam Amidopropyldimethyl Betaine | Emulsifier/ Conditioner |
| 6. Cetearyl Alcohol | 0.75 | Cetearyl Alcohol | Thickener |
| 7. Meadowlactone | 2.00 | Meadowfoam Delta Lactone | Active Agent |
| 8. Fancol ® VB | 2.50 | *Limnanthes Alba* (Meadowfoam) Seed Oil, *Butyrospermum ParkiiI* (Shea Butter) Extract | Emollient/ Conditioner |
| 9. *Camelia Sinersis* Extract | 0.10 | *Camelia Sinersis* Extract | Stabilizer |
| 10. DMDM Hydantoin | 0.40 | DMDM Hydantoin | Preservative |

Preparative Procedure:

Ingredients 1., 2. and 3. are heated to 75° C. in a main vessel. Separately, ingredients 4., 5., 6., 7. and 8. are heated to 80° C., and added to the water phase. The ingredients are mixed well for 15 minutes using slow agitation and cooled to 45° C. Ingredients 9. and 10. are added and mixed until the mixture is homogenous. The mixture is cooled to 30° C. and then poured into containers.

Ingredients 5., 7. and 8. are commercially available from The Fanning Corporation (Chicago, Ill.).

Appearance/Characteristics:

White Lotion pH: 4.5 0-5.50

Viscosity: 5,000-8000 cps @ 25 C.

EXAMPLE 13

Skin Moisturizing Lotion

| Ingredient | Weight % | INCI Name | Function |
|---|---|---|---|
| 1. Deionized Water | q.s | Water | Diluent |
| 2. Propylene Glycol, USP | 5.00 | Propylene Glycol | Humectant |
| 3. Fanwax ® SEW-P | 4.50 | Emulsifying Wax, NF | Emulsifier |
| 4. Cetearyl Alcohol | 1.00 | Cetearyl Alcohol | Conditioner |
| 5. Mineral Oil, 70vs | 7.50 | Mineral Oil | Emollient |
| 6. Meadowlactone | 2.50 | Meadowfoam Delta Lactone | Active Agent |
| 7. Phenoxyethanol, Methylparaben, Ethylparaben, Propylparaben, and Butylparaben | 1.00 | Phenoxyethanol, Methylparaben, Ethylparaben, Propylparaben, and Butylparaben | Preservative |
| 8. Perfume | 0.25 | Fragrance | Aroma |

Preparative Procedure:

Ingredients 1. and 2. are heated to 75° C. Separately, ingredients 3., 4., 5., 6. and 7. are heated to 75° C. These ingredients are combined with the water phase slowly, and the mixture is mixed well and cooled to 45° C. Ingredient 8. is added, and cooling is continued to 30° C. with good agitation.

Ingredients 3. and 6. are commercially available from The Fanning Corporation (Chicago, Ill.).

Appearance/Characteristics:

Off white, thick lotion pH: 5-6 @ 25° C. Viscosity: 7,000-10,000 cps. @ 25° C.

EXAMPLE 14

Skin Softening Cream

| Ingredient | Weight % | INCI Name | Function |
|---|---|---|---|
| 1. Deionized Water | q.s | Water | Diluent |
| 2. Glycerine, 99.0% | 4.00 | Glycerin | Humectant |
| 3. Fanwax ® Sew-P | 4.50 | Emulsifying Wax, NF | Emulsifier |
| 4. Cetearyl Alcohol | 2.00 | Cetearyl Alcohol | Conditioner |
| 5. Mineral Oil, 70vs | 8.00 | Mineral Oil | Emollient |
| 6. Fancor ® Lanolin, USP | 3.00 | Lanolin | Conditioner/ Emollient |
| 7. Meadowlactone | 2.00 | Meadowfoam Delta Lactone | Active Agent |
| 8. Phenoxyethanol, Methylparaben, Ethylparaben, Propylparaben, and Butylparaben | 1.00 | Phenoxyethanol, Methylparaben, Ethylparaben, Propylparaben, and Butylparaben | Preservative |
| 9. Fragrance | 0.25 | Fragrance | Aroma |

Preparative Procedure:

Ingredients 1. and 2. were heated to 75° C. Separately, ingredients 3., 4., 5., 6. and 7. were heated to 75° C. These ingredients were combined with the water phase slowly and the mixture was mixed well and cooled to 45° C. Ingredients 8. and 9. were added, and the mixture was cooled to 30° C. with good agitation.

Ingredients 3., 6. and 7. are commercially available from The Fanning Corporation (Chicago, Ill.).

Appearance/Characteristics:

Off white, thick cream pH: 5-6 @25° C.

Viscosity: 20,000-25,000 cps. @ 25° C.

EXAMPLE 15

Body Oil

| Ingredient | Weight % | INCI Name | Function |
|---|---|---|---|
| 1. EmCon ® SAF | 93.47 | Safflower Oil | Skin Conditioner |
| 2. Fancol ® CH | 0.03 | Cholesterol | Skin Toning Conditioner |
| 3. Meadowlactone | 1.00 | Meadowfoam Delta Lactone | Active Agent |
| 4. Fanoliv ® ActivE | 3.00 | Olive (*Olea Europa*) Oil Unsaponifiables | Emollient/ Anti-oxidant |
| 5. Fancol ® Karite Extract | 2.00 | *Butyrospermum Parkii* (Shea Butter) Fruit | Moisturizer |
| 6. Phenoxyethanol | 0.40 | Phenoxyethanol | Preservative |
| 7. Fragrance | 0.10 | Fragrance | Perfume |

Preparative Procedure:

Ingredient 1. was heated to 60° C. Ingredients 2. and 3. were mixed in together until they were well dissolved and uniform. The mixture was cooled to 45° C. Ingredients 4., 5., 6. and 7. were added to the mixture and mixed until homogenous, resulting in a very clear oily liquid.

Ingredients 1., 2., 3., 4. and 5. are commercially available from The Fanning Corporation (Chicago, Ill.).

Appearance: Sparkling clear, slightly yellow oily liquid

EXAMPLE 16

Hair Relaxer Base with and without Meadowlactone

| Ingredient | INCI Name | Weight % (with Meadowlactone) | Weight % (without Meadowlactone) |
|---|---|---|---|
| Phase I | | | |
| 1. Deionized Water | Water | 46.20 | 48.20 |
| 2. Propylene Glycol | Propylene Glycol | 2.00 | 2.00 |
| Phase II | | | |
| 3. Petrolatum | Petrolatum | 14.00 | 14.00 |
| 4. Mineral Oil, 70vs | Mineral Oil | 16.00 | 16.00 |
| 5. Fanwax ® SEW-P | Emulsifying Wax, NF | 11.00 | 11.00 |
| 6. Fancol ® LA-15 | Laneth-15 | 1.00 | 1.00 |
| 7. Lan-Aqua-Sol ™ 75:100 | PEG-75 Lanolin | 0.50 | 0.50 |
| 8. Meadowlactone | Meadowfoam Delta Lactone | 2.00 | — |
| Phase III | | | |
| 9. 50% Sodium Hydroxide | Sodium Hydroxide | 4.80 | 4.80 |
| 10. Deionized water | Water | 2.50 | 2.50 |

Preparative Procedure:

Phase I and phase II were added into separate containers, and heating was begun to heat each phase to 80° C. Once the phases reached 80° C., phase II was added to phase I and mixed strongly with good shear for 15 minutes. Heating was stopped, and the mixture was mixed moderately to allow entrapped air to dissipate completely while air cooling to about 55 C. Phase III was premixed and set aside. The initial mixture was force cooled to 30° C. with a sweep mixer. When it reached about 30° C., the premixed Phase III was added slowly with good chilling water and sweep mixing was continued. When uniform, samples were taken at 25° C., assayed and homogenized to containers.

Ingredients 5., 6., 7. and 8. are commercially available from The Fanning Corporation (Chicago, Ill.).

Appearance/Characteristics:

| white viscous cream | | |
|---|---|---|
| % NaOH | 2.35-2.40% | 2.35-2.40% |
| Viscosity, cps@25C, LVT 4/0.6; 5" Factor: 10000 | 370,000 cps | 290,000 cps |

EXAMPLE 17

Hair Crème Instant Conditioner

| Ingredient | Weight % | INCI Name | Function |
|---|---|---|---|
| 1. Deionized Water | q.s. | Water | Diluent |
| 2. Methylparaben, Propylparaben | 0.25 | Methylparaben, Propylparaben | Preservative |
| 3. Hydroxyethylcellulose | 0.50 | Hydroxyethylcellulose | Thickener/ Slip |

Hair Crème Instant Conditioner

| Ingredient | Weight % | INCI Name | Function |
|---|---|---|---|
| 4. Propylene Glycol | 3.00 | Propylene Glycol | Humectant |
| 5. Fanwax ® Sew-P | 5.50 | Emulsifying Wax NF | Emulsifier |
| 6. Cetearyl Alcohol | 6.00 | Cetearyl Alcohol | Thickener/Conditioner |
| 7. Fancor ® Abyssinian Oil | 5.00 | *Crambe Abyssinica* Seed Oil | Emollient/Conditioner |
| 8. Fancorsil ® LIM-2 | 1.00 | Dimethicone PEG-8 Meadowfoamate | Conditioner/Strengthener |
| 9. Meadowquat ® HG-70 | 3.00 | PEG-2 Dimeadow-foamamidoethylmonium Methosulfate | Conditioner/Shine |
| 10. Meadowlactone | 0.50 | Meadowfoam Delta Lactone | Active Agent |
| 11. DMDM Hydantoin | 0.40 | DMDM Hydantoin | Preservative |
| 12. Lactic Acid, 86% | 0.04 | Lactic Acid | pH Adjuster |

Preparative Procedure:

Ingredients 1., 2., 3. and 4. are heated to 75° C. in a main vessel. Ingredients 5., 6., 7. and 8 are added into the batch at 75° C., and the ingredients are mixed vigorously for 10 minutes. With slow agitation, ingredients 9. and 10. are added and mixed, and all foam is allowed to dissipate. The mixture is cooled to 45° C. and ingredient 11. is added with continued mixing until homogenous. If necessary, the pH is adjusted with ingredient 12. Cooling is continued to 25° C. The product is pumped through an in-line homomixer into containers.

Ingredients 5., 7., 8., 9. and 10. are commercially available from The Fanning Corporation (Chicago, Ill.).

Appearance/Characteristics:

Off white thick crème.
pH: 4.2-4.8
Viscosity: 50,000-8000 cps @ 25° C.

EXAMPLE 18

Preparative Procedure:

Ingredients 1., 2. and 3. were heated to 75° C. Ingredient 4. was added and the ingredients were mixed strongly for 10 minutes. The heat was terminated, and the mixture was dearated and air cooled to 60° C. The mixture was then force cooled to 30° C. Ingredients 5. and 6. were premixed and added to the mixture, and the mixture was mixed moderately until uniform. The pH was adjusted with ingredient 6. when necessary.

Ingredients 3. and 4. are commercially available from The Fanning Corporation (Chicago, Ill.).

Characteristics:

pH: 3.21
Viscosity: 4200 cps
Hydrogen Peroxide: 6.23%

Hair Color Developer, 20 Volume

| Ingredient | Weight % | INCI Name | Function |
|---|---|---|---|
| 1. Deionized Water | q.s. | Water | Diluent |
| 2. Pentasodium Pentetate | 0.25 | Pentasodium Pentetate | Chelating Agent |
| 3. Meadowlactone | 1.00 | Meadowfoam Delta Lactone | Active Agent |
| 4. Fancor ® Uni-Embase | 5.75 | Cetearyl Alcohol, Polysorbate 65, Dimethicone PEG-8 Meadowfoamate, Meadowfoam Amidopropyldimethyl Betaine | Emulsifier/Thickener |
| 5. Hydrogen Peroxide, 35% | 17.50 | Hydrogen Peroxide | Oxidizer |
| 6. Phosphoric Acid, 86% | 0.75 | Phosphoric Acid | pH Adjuster |

EXAMPLE 19

Hair Conditioner Cream

| Ingredient | Weight % | INCI Name | Function |
|---|---|---|---|
| 1. Deionized Water | 74.10 | Water | Diluent |
| 2. Propylene Glycol | 3.00 | Propylene glycol | Humectant |
| 3. Mineral Oil | 10.00 | Mineral Oil | Emollient |
| 4. Fanwax ® Sew-P | 5.50 | Emulsifying Wax, NF | Emulsifier |
| 5. Meadowlactone | 5.00 | Meadowfoam Delta Lactone | Active Agent |
| 6. Cetearyl Alcohol | 2.00 | Cetearyl Alcohol | Thickener |
| 7. DMDM Hydantoin | 0.40 | DMDM Hydantoin | Preservative |

Preparative Procedure:

Ingredients 1. and 2. were heated to 75° C. in a main vessel. Separately, ingredients 3., 4., 5. and 6. were heated to 80° C., and added to the water phase. These ingredients were mixed well for 15 minutes with slow agitation and cooled to 50° C. Ingredient 7. was added and the mixture was mixed until homogenous. Cooling was continued to 30° C.

Ingredients 4. and 5. are commercially available from The Fanning Corporation (Chicago, Ill.).

Characteristics:
pH: 6.0-7.0
Viscosity: 10,000-20,000 cps

EXAMPLE 20

Gel Shampoo for Normal Hair

| Ingredient | Weight % | INCI Name | Function |
|---|---|---|---|
| 1. Deionized Water | 55.10 | Water | Diluent |
| 2. Ammonium Laureth Sulfate | 25.00 | Ammonium Laureth Sulfate | Surfactant |
| 3. Ammonium Lauryl Sulfate | 15.00 | Ammonium Lauryl Sulfate | Surfactant |
| 4. Cocamide MEA | 2.00 | Cocamide MEA | Foam Stabilizer |
| 5. Meadowlactone | 2.00 | Meadowfoam Delta Lactone | Active Agent |
| 6. DMDM Hydantoin | 0.40 | DMDM Hydantoin | Preservative |
| 7. Sodium Hydroxide, 50% | q.s | Sodium Hydroxide | ph Adjuster |

Preparative Procedure:

Ingredient 1. was charged into a main vessel. Ingredients 2. and 3. were added, and the mixture was heated to 60° C. At 60° C., and when the mixture was homogeneous, ingredients 4. and 5. were added. The mixture was mixed well and cooled to 45° C. Ingredient 6. was added and the mixture was agitated well. The mixture was cooled to 30° C. and the pH was adjusted with ingredient 7. to a desired pH.

Appearance/Characteristics:
pH: 7.3-8.07
Viscosity: 75-90M LVT 4/6 RPM, Factor: 1000
Clear thick Viscose Gel

EXAMPLE 21

Sodium Hair Relaxer

| Ingredient | INCI Name | Weight % | Function |
|---|---|---|---|
| Phase I | | | |
| 1. Deionized Water | Water | 47.60 | Diluent |
| 2. Propylene Glycol | Proplylene Glycol | 2.50 | Humectant |
| Phase II | | | |
| 3. Petrolatum | Petrolatum | 14.00 | Emollient |
| 4. Mineral Oil, 70vs | Mineral Oil | 16.00 | Lubricity |
| 5. Fanwax ® SEW-P | Emulsifying Wax, NF | 11.00 | Emulsifier |
| 6. Fancol ® LA-15 | Laneth-15 | 1.00 | Conditioner |
| 7. Lan-Aqua-Sol ™ 75:100 | PEG-75 Lanolin | 0.50 | Conditioner |
| 8. Meadowlactone | Meadowfoam Delta Lactone | 1.00 | Active Agent |
| Phase III | | | |
| 9. 50% Sodium Hydroxide | Sodium Hydroxide | 4.40 | Activity |
| 10. Deionized water | Water | 2.50 | Diluent |

Preparative Procedure:

Phase I and phase II were added into separate containers, and heating was begun to heat each phase to 80° C. Once the phases reached 80° C., phase II was added to phase I and mixed strongly for 15 minutes. Heating was stopped, and the mixture was mixed moderately while air cooling to about 55° C. Phase III was premixed and set aside. The initial mixture was force cooled to 30° C. with a sweep mixer. The premixed Phase III was added slowly to the mixture with good chilling water. When uniform, samples were taken at 25° C., assayed and homogenized to containers.

Appearance/Characteristics:

| | |
|---|---|
| white viscous cream | |
| % NaOH | 2.15-2.20% |
| Viscosity, cps@25C, LVT 4/0.6; 5" Factor: 10000 | 250,000-350,000 cps |

EXAMPLE 22

Shampoos/Body Washes

| Ingredient | INCI Name | Weight % Formula A | Weight % Formula B |
|---|---|---|---|
| Phase A | | | |
| 1. D.I. Water | Water | q.s | q.s |
| 2. Ammonium Laureth Sulfate | Ammonium Laureth Sulfate | 9.00 | 9.00 |
| 3. Ammonium Laurel Sulfate | Ammonium Laurel Sulfate | 27.00 | 27.00 |
| 4. Cocamide Mea | Cocamide Mea | 0.50 | 0.50 |
| 5. Betafan ® M | Meadowfoam, Amidopropyldimethyl Betaine | 3.00 | 3.00 |
| 6. DMDM Hydantoin | DMDM Hydantoin | 0.4 | 0.4 |
| 7. Sodium Chloride | Sodium Chloride | 0.25 | 0.25 |

-continued

Shampoos/Body Washes

| Ingredient | INCI Name | Weight % Formula A | Weight % Formula B |
|---|---|---|---|
| | Phase B | | |
| 8. Meadowlactone | Meadowfoam Delta Lactone | 3.00 | 3.00 |
| 9. Sodium Hydroxide, 50% | Sodium Hydroxide | | 0.65 |

Preparative Procedure:

Phase A was warmed to 45° C. Phase B was added, and the mixture was mixed well until homogenous and then cooled to 30-35° C. The pH was adjusted with sodium hydroxide to the desired specification (Formula B). The product was poured into containers.

| Appearance/Characteristics: | Formula A | Formula B |
|---|---|---|
| pH | 5.50 | 8.60 |
| Viscosity, cps@ RT | 3200 | 400 |
| Appearance | White/translucent Cloudy | White Clear Liquid |

While the present invention has been described herein with specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as described and claimed herein, and that the invention be limited only by the scope of the claims which follow, and that such claims be interpreted as broadly as is reasonable.

Throughout this document, various books, patents, journal articles, web sites and other publications have been cited. The entireties of each of these books, patents, journal articles, web sites and other publications are hereby incorporated by reference herein.

What is claimed is:

1. A method for treating wrinkles of a mammal's skin comprising topically applying to the skin at least three applications on a regular basis of a composition comprising:
   (a) a Meadowlactone in an amount that is effective for treating wrinkles of the skin, wherein the Meadowlactone has the structure:

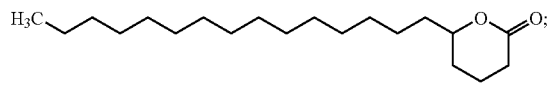

and (b) a cosmetically acceptable base in an amount that is effective for acting as a carrier vehicle for the Meadowlactone;

wherein the amount of the composition that is applied to the skin is an amount that is effective for treating wrinkles of the mammal's skin; and wherein the pH of the composition ranges from about 2 to about 11.

2. The method of claim 1 wherein the amount of the Meadowlactone ranges from about 0.1 to about 20 weight percent of the total weight of the composition.

3. The method of claim 2 wherein the amount of the Meadowlactone ranges from about 1 to about 5 weight percent of the total weight of the composition.

4. The method of claim 3 wherein the amount of the Meadowlactone ranges from about 1.5 to about 4.5 weight percent of the total weight of the composition.

5. The method of claim 4 wherein the amount of the Meadowlactone ranges from about 2.0 to about 4.0 weight percent of the total weight of the composition.

6. The method of claim 5 wherein the amount of the Meadowlactone ranges from about 2.5 to about 3.5 weight percent of the total weight of the composition.

7. The method of claim 2 wherein the amount of the Meadowlactone ranges from about 0.1 to about 4 weight percent of the total weight of the composition.

8. The method of claim 2 wherein the amount of the Meadowlactone ranges from about 6 to about 20 weight percent of the total weight of the composition.

9. The method of claim 1 wherein the composition is a leave-on type composition.

10. The method of claim 1 wherein the cosmetically acceptable base is a cream base that contains the following ingredients, and weight percents thereof:

| | |
|---|---|
| Deionized water | 87.0-90.0% |
| Self-emulsifying wax N.F. | 7.75% |
| Methylparaben/propylparaben | 0.25%. |

11. The method of claim 2 wherein the composition is a leave-on type composition and the cosmetically acceptable base is a cream base that contains the following ingredients, and weight percents thereof:

| | |
|---|---|
| Deionized water | 87.0-90.0% |
| Self-emulsifying wax N.F. | 7.75% |
| Methylparaben/propylparaben | 0.25%. |

12. The method of claim 1 wherein the composition is a rinse-off type composition, and wherein the composition is not rinsed off of, or otherwise removed from, the skin after an application of the composition to the skin for a period of time that is sufficient for conditioning the skin.

13. The method of claim 12 wherein the composition is not rinsed off of, or otherwise removed from, the skin after an application of the composition to the skin for a period of at least about six minutes after such application.

14. The method of claim 1 wherein the composition contains the following ingredients, and weight percents thereof:

| | |
|---|---|
| Deionized water | 90.0% |
| Self-emulsifying wax N.F. | 7.75% |
| Methylparaben/propylparaben | 0.25% |
| Meadowestolide | 2.0%. |

15. The method of claim 1 wherein the amount of the composition that is applied to the skin per each application ranges from about 1 to about 20 g or ml.

16. The method of claim 15 wherein the amount of the composition that is applied to the skin per each application ranges from about 2 to about 12 g or ml.

17. The method of claim 16 wherein the amount of the composition that is applied to the skin per each application ranges from about 3 to about 8 g or ml.

18. The method of claim 17 wherein the amount of the composition that is applied to the skin per each application ranges from about 4 to about 6 g or ml.

19. The method of claim 18 wherein the amount of the composition that is applied to the skin per each application is about 5 g or ml.

20. The method of claim 14 wherein the amount of the composition that is applied to the skin per each application ranges from about 1 to about 20 g or ml.

21. The method of claim 20 wherein the amount of the composition that is applied to the skin per each application ranges from about 2 to about 12 g or ml.

22. The method of claim 1 wherein three or more applications of the composition are applied to the skin of the mammal over a period of time ranging from about three hours to about three days.

23. The method of claim 1 wherein four or more applications of the composition are applied to the skin of the mammal over a period of time ranging from about four hours to about four days.

24. The method of claim 1 wherein five or more applications of the composition are applied to the skin of the mammal over a period of time ranging from about five hours to about five days.

25. The method of claim 1 wherein six or more applications of the composition are applied to the skin of the mammal over a period of time ranging from about six hours to about six days.

26. The method of claim 1 wherein seven or more applications of the composition are applied to the skin of the mammal over a period of time ranging from about seven hours to about seven days.

27. The method of claim 1 wherein eight or more applications of the composition are applied to the skin of the mammal over a period of time ranging from about eight hours to about eight days.

28. The method of claim 1 wherein nine or more applications of the composition are applied to the skin of the mammal over a period of time ranging from about nine hours to about nine days.

29. The method of claim 1 wherein ten or more applications of the composition are applied to the skin of the mammal over a period of time ranging from about ten hours to about ten days.

30. The method of claim 1 wherein eleven or more applications of the composition are applied to the skin of the mammal over a period of time ranging from about eleven hours to about eleven days.

31. The method of claim 1 wherein twelve or more applications of the composition are applied to the skin of the mammal over a period of time ranging from about twelve hours to about twelve days.

32. The method of claim 1 wherein thirteen or more applications of the composition are applied to the skin of the mammal over a period of time ranging from about thirteen hours to about thirteen days.

33. The method of claim 1 wherein fourteen or more applications of the composition are applied to the skin of the mammal over a period of time ranging from about fourteen hours to about fourteen days.

34. The method of claim 1 wherein fifteen or more applications of the composition are applied to the skin of the mammal over a period of time ranging from about fifteen hours to about fifteen days.

35. The method of claim 1 wherein sixteen or more applications of the composition are applied to the skin of the mammal over a period of time ranging from about sixteen hours to about sixteen days.

36. The method of claim 1 wherein seventeen or more applications of the composition are applied to the skin of the mammal over a period of time ranging from about seventeen hours to about seventeen days.

37. The method of claim 1 wherein eighteen or more applications of the composition are applied to the skin of the mammal over a period of time ranging from about eighteen hours to about eighteen days.

38. The method of claim 1 wherein nineteen or more applications of the composition are applied to the skin of the mammal over a period of time ranging from about nineteen hours to about nineteen days.

39. The method of claim 1 wherein twenty or more applications of the composition are applied to the skin of the mammal over a period of time ranging from about twenty hours to about twenty days.

40. The method of claim 1 wherein twenty one or more applications of the composition are applied to the skin of the mammal over a period of time ranging from about twenty one hours to about twenty one days.

41. The method of claim 1 wherein twenty two or more applications of the composition are applied to the skin of the mammal over a period of time ranging from about twenty two hours to about twenty two days.

42. The method of claim 1 wherein twenty three or more applications of the composition are applied to the skin of the mammal over a period of time ranging from about twenty three hours to about twenty three days.

43. The method of claim 1 wherein twenty four or more applications of the composition are applied to the skin of the mammal over a period of time ranging from about twenty four hours to about twenty four days.

44. The method of claim 1 wherein from about twenty five to about sixty applications of the composition are applied to the skin of the mammal over a period of time ranging from about twenty five hours to about fifty days.

45. The method of claim 1 wherein from about sixty one to about one hundred and twenty applications of the composition are applied to the skin of the mammal over a period of time ranging from about sixty one hours to about sixty days.

46. The method of claim 1 wherein from about one hundred and twenty one to about two hundred and forty applications of the composition are applied to the skin of the mammal over a period of time ranging from about one hundred and twenty one hours to about eighty days.

47. The method of claim 1 wherein the composition does not include a hydroxyphenyltriazine compound or an HDI/trimethylol hexyl-lactone crosspolymer.

48. The method of claim 1 wherein the composition does not include a bioactive glass, or a composition derived from an aqueous extract of bloactive glass.

49. The method of claim 1 wherein the composition does not include cystine, a cystine derivative, or a salt thereof.

50. The method of claim 1 wherein the composition does not include meadowfoam oil or any components of meadowfoam oil.

51. A method for treating wrinkles of a mammal's skin comprising topically applying to the skin at least three applications on a regular basis of a composition consisting of:

(a) a Meadowlactone in an amount that is effective for treating wrinkles of the skin, wherein the Meadowlactone has the structure:

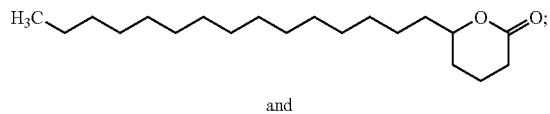

and (b) a cosmetically acceptable base in an amount that is effective for acting as a carrier vehicle for the Meadowlactone;

wherein the amount of the composition that is applied to the skin is an amount that is effective for of the mammal's skin;

wherein the pH of the composition ranges from about 2 to about 11.

* * * * *